US007078542B2

(12) United States Patent
Jen et al.

(10) Patent No.: US 7,078,542 B2
(45) Date of Patent: Jul. 18, 2006

(54) NONLINEAR OPTICAL COMPOUNDS AND METHODS FOR THEIR PREPARATION

(75) Inventors: Kwan-Yue Jen, Kenmore, WA (US); Hong Ma, Seattle, WA (US); Sen Liu, Seattle, WA (US); Larry R Dalton, Silverdale, WA (US)

(73) Assignee: University of Washington, Seattle, WA (US)

( * ) Notice: Subject to any disclaimer, the term of this patent is extended or adjusted under 35 U.S.C. 154(b) by 0 days.

(21) Appl. No.: 10/934,964

(22) Filed: Sep. 3, 2004

(65) Prior Publication Data

US 2005/0023507 A1     Feb. 3, 2005

Related U.S. Application Data

(62) Division of application No. 10/347,117, filed on Jan. 15, 2003.

(51) Int. Cl.
C07D 307/26 (2006.01)
C07D 307/30 (2006.01)
C07D 307/02 (2006.01)

(52) U.S. Cl. ............... 549/474; 549/481; 549/483; 549/504; 549/507; 549/472

(58) Field of Classification Search ............... 252/582, 252/583, 586; 549/462, 467, 472, 474, 481, 549/483, 504, 507
See application file for complete search history.

(56) References Cited

U.S. PATENT DOCUMENTS

| | | | |
|---|---|---|---|
| 5,432,286 | A | 7/1995 | Cabrera et al. |
| 5,514,799 | A | 5/1996 | Varanasi et al. |
| 5,676,884 | A | 10/1997 | Tiers et al. |
| 5,679,763 | A | 10/1997 | Jen et al. |
| 5,693,734 | A | 12/1997 | Herzig et al. |
| 5,718,845 | A | 2/1998 | Drost et al. |
| 5,738,806 | A | 4/1998 | Beckmann et al. |
| 5,804,101 | A | 9/1998 | Marder et al. |
| 5,808,100 | A | 9/1998 | Momoda et al. |
| 6,067,186 | A | 5/2000 | Dalton et al. |
| 6,184,540 | B1 | 2/2001 | Chmii et al. |
| 6,211,374 | B1 | 4/2001 | Ippoliti |
| 6,281,366 | B1 | 8/2001 | Frigoli et al. |
| 6,348,992 | B1 | 2/2002 | Zhang et al. |
| 6,361,717 | B1 | 3/2002 | Dalton et al. |
| 6,393,190 | B1 * | 5/2002 | He et al. .................... 385/130 |
| 2002/0084446 | A1 | 7/2002 | Dalton et al. |
| 2002/0160282 | A1 | 10/2002 | Huang et al. |

FOREIGN PATENT DOCUMENTS

| | | |
|---|---|---|
| WO | WO 00/009613 A2 | 2/2000 |
| WO | WO 01/53746 A1 | 7/2001 |
| WO | WO 01/56462 A1 | 8/2001 |
| WO | WO 01/77749 A1 | 10/2001 |
| WO | WO 01/79750 A1 | 10/2001 |
| WO | WO 02/08215 A1 | 1/2002 |
| WO | WO 02/14305 A2 | 2/2002 |
| WO | WO 02/29488 A1 | 4/2002 |
| WO | WO 02/37173 A2 | 5/2002 |

OTHER PUBLICATIONS

CA 138: 24608, 2002.*
Dalton, L., "Polymeric Electro-Optic Materials: Optimization of Electro-Optic Activity, Minimization of Optical Loss, and Fine-Tuning of Device Performance," *Opt. Eng.* 39(3):589-595, Mar. 2000.
Dalton, L.R., et al, "From Molecules to Opto-Chips: Organic Electro-Optic Materials," *J. Mater. Chem.* 9:1905-1920, 1999.
He, M., et al., "Synthesis of Chromophores with Extremely High Electro-Optic Activity. 1. Thiophene-Bridge-Based Chromophores," *Chem. Mater.* 14:4662-4668, 2002.
Luo, J., et al., "Design, Synthesis, and Properties of Highly Efficient Side-Chain Dendronized Nonlinear Optical Polymers for Electro-Optics," *Adv. Mater.* 14(23):1763-1768, Dec. 3, 2002.
Ma, H., et al., "Polymer-Based Optical Waveguides: Materials, Processing, and Devices," *Adv. Mater.* 14(19):1339-1365, Oct. 2, 2002.
Melikian, G., et al., "Synthesis of Substituted Dicyanomethylendihydrofurans," *Synth. Commun.* 25(19):3045-3051, 1995.
Villemin, D., and L. Liao, "Rapid and Efficient Synthesis of 2-[3-Cyano-4-(2-Aryliden)-5,5-Dimethyl-5H-Furan-2-Ylidene]-Malononitrile Under Focused Microwave Irradiation," *Synth. Commun.* 31(11):1771-1780, 2001.

* cited by examiner

*Primary Examiner*—Shean C Wu
(74) *Attorney, Agent, or Firm*—Christensen O'Connor Johnson Kindness PLLC

(57) ABSTRACT

Nonlinear optically active compounds, methods for making nonlinear optically active compounds, compounds useful for making nonlinear optically active compounds, methods for making compounds useful for making nonlinear optically active compounds, macrostructures that include nonlinear optically active components, and devices including the nonlinear optically active compounds and the macrostructures.

12 Claims, 19 Drawing Sheets

$R_1$, $R_2$:

$CH_3$, $CF_3$, $(CH_2)_nOCH_2OCH_3$, $(CH_2)_nOCOCH_3$, $(CH_2)_nOSi(Me)_2C(Me)_3$, n=3-8, $A_1$, $A_2$, $A_3$:

-CN, -NO$_2$, -COOEt, -SO$_2$CF$_3$, -SO$_2$Ph,

# NONLINEAR OPTICAL COMPOUNDS AND METHODS FOR THEIR PREPARATION

CROSS-REFERENCE TO RELATED APPLICATION

This application is a division of U.S. patent application Ser. No. 10/347,117, filed Jan. 15, 2003, which is incorporated herein by reference in its entirety.

STATEMENT REGARDING FEDERALLY SPONSORED RESEARCH OR GOVERNMENT DEVELOPMENT

The invention was made by an agency of the United States Government or under a contract with an agency of the United States Government. The name of the U.S. Government agency is the Air Force Office of Scientific Research and the Government contract number is F49620-00- 1-0060. The government has certain rights in the invention.

FIELD OF THE INVENTION

The present invention relates to nonlinear optically active compounds, methods for making nonlinear optically active compounds, macrostructures that include nonlinear optically active components, and devices including nonlinear optically active compounds and macrostructures that include nonlinear optically active components.

BACKGROUND OF THE INVENTION

Electrical signals can be encoded onto fiber-optic transmissions by electro-optic modulators. These modulators include electro-optic materials having highly polarizable electrons. When these materials are subject to an electric field, their polarization changes dramatically resulting in an increase in the index of refraction of the material and an accompanying decrease in the velocity of light traveling through the material. This electric field-dependent index of refraction can be used to encode electric signals onto optical signals. Uses include, for example, switching optical signals and steering light beams.

A variety of electro-optic materials have been utilized for use in electro-optic devices. Among these materials are inorganic materials such as lithium niobate, semiconductor materials such as gallium arsenide, organic crystalline materials, and electrically poled polymer films that include organic chromophores. A review of nonlinear optical materials is provided in L. Dalton, "Nonlinear Optical Materials," *Kirk-Othmer Encyclopedia of Chemical Technology*, 4$^{th}$ ed., Vol. 17, John Wiley & Sons, New York, 1995, pp. 288–302.

In contrast to inorganic materials in which polar optical lattice vibrations diminish effectiveness, the optical properties of organic nonlinear optical materials depend primarily on the hyperpolarizability of their electrons without a significant adverse contribution from the lattice polarizability. Thus, organic nonlinear optical materials offer advantages for ultrafast electro-optic modulation and switching.

Lithium niobate, a common material currently utilized in electro-optic devices, has an electro-optic coefficient of about 35 pm/V resulting in a typical drive voltage of about 5 volts. Drive voltage ($V_\pi$) refers to the voltage that produces a $\pi$ phase shift of light. Lithium niobate has a high dielectric constant ($\epsilon=28$), which results in a mismatch of electrical and optical waves propagating in the material. The mismatch necessitates a short interaction length, which makes drive voltage reduction through increasing device length unfeasible, thereby limiting the device's bandwidth. Recent lithium niobate modulators have been demonstrated to operate at a bandwidth of over 70 GHz.

Electro-optic poled polymers have also been utilized as modulating materials. Their advantages include their applicability to thin-film waveguiding structures, which are relatively easily fabricated and compatible with existing microelectronic processing. These polymers incorporate organic nonlinear optically active molecules to effect modulation. Because organic materials have low dielectric constants and satisfy the condition that $n^2=\epsilon$, where n is the index of refraction and $\epsilon$ is the dielectric constant, organic electro-optic will have wide bandwidths. The dielectric constant of these materials ($\epsilon=2.5–4$) relatively closely matches the propagating electrical and optical waves, which provides for a drive voltage in the range of about 1–2 volts and a bandwidth greater than 100 GHz.

Advantages of organic nonlinear optical materials include a bandwidth in excess of 100 GHz/cm device and ease of integration with semiconductor devices. See Dalton, L., et al., "Synthesis and Processing of Improved Organic Second-Order Nonlinear Optical Materials for Applications in Photonics," *Chemistry of Materials* 7(6):1060–1081, 1995. In contrast to inorganic materials, these organic materials can be systematically modified to improve electro-optic activity by the design and development of new organic materials and by the development of improved processing methods. See Dalton. L., et al., "The Role of London Forces in Defining Noncentrosymmetric Order of High Dipole Moment-High Hyperpolarizability Chromophores in Electrically Poled Polymeric Films," *Proceedings of the National Academy of Sciences USA* 94:4842–4847, 1997.

For an organic nonlinear optical material to be suitable for electro-optic applications, the material should have a large molecular optical nonlinearity, referred to as hyperpolarizability ($\beta$), and a large dipole moment ($\mu$). A commonly figure of merit used to compare materials is the value $\mu\beta$. See Dalton et al. (1997). Organic materials having $\mu\beta$ values greater than about $15,000 \times 10^{-48}$ esu that also satisfy the desired thermal and chemical stability and low optical loss at operating wavelengths have only recently been prepared. See Dalton, et al., "New Class of High Hyperpolarizability Organic Chromophores and Process for Synthesizing the Same," WO 00/09613. However, materials characterized as having such large $\mu\beta$ values suffer from large intermolecular electrostatic interactions that lead to intermolecular aggregation resulting in light scattering and unacceptably high values of optical loss. See Dalton et al. (1997). A chromophore's optical nonlinearity ($\mu\beta$) can be measured as described in Dalton, L., et al., "Importance of Intermolecular Interactions in the Nonlinear Optical Properties of Poled Polymers," *Applied Physics Letters* 76(11):1368–1370, 2000. A chromophore's electro-optic coefficient ($r_{33}$) can be measured in a polymer matrix using attenuated total reflection (ATR) technique at telecommunication wavelengths of 1.3 or 1.55 µm. A representative method for measuring the electro-optic coefficient is described in Dalton, L., et al., "Importance of Intermolecular Interactions in the Nonlinear Optical Properties of Poled Polymers," *Applied Physics Letters* 76(11):1368–1370, 2000.

Many molecules can be prepared having high hyperpolarizability values, however their utility in electro-optic devices is often diminished by the inability to incorporate these molecules into a host material with sufficient noncentrosymmetric molecular alignment to provide a device with acceptable electro-optic activity. Molecules with high hyperpolarizability typically exhibit strong dipole-dipole interactions in solution or other host material that makes it difficult, to achieve a high degree of noncentrosymmetric order without minimizing undesirable spatially anisotropic intermolecular electrostatic interactions.

Chromophore performance is dependent on chromophore shape. See Dalton, L., et al., "Low (Sub-1-Volt) Halfwave Voltage Polymeric Electro-optic Modulators Achieved by Controlling Chromophore Shape," *Science* 288:119–122, 2000.

Chemical, thermal, and photochemical stabilities are imparted to the chromophores through their chemical structure and substituent choice. For example, in certain embodiments, the chromophore's active hydrogens are substituted with groups (e.g., alkyl, fluorine) to impart increased stability to the chromophore.

Thus, the effectiveness of organic nonlinear optical materials having high hyperpolarizability and large dipole moments can be limited by the tendency of these materials to aggregate when processed into electro-optic devices. The result is a loss of optical nonlinearity. Accordingly, improved nonlinear optically active materials having large hyperpolarizabilities and large dipole moments and that, when employed in electro-optic devices, exhibit large electro-optic coefficients may be advantageous for many applications.

For the fabrication of practical electro-optical (E-O) devices, critical material requirements, such as large E-O coefficients, high stability (thermal, chemical, photochemical, and mechanical), and low optical loss, need to be simultaneously optimized. In the past decade, a large number of highly active nonlinear optical (NLO) chromophores have been synthesized, and some of these exhibit very large macroscopic optical nonlinearities in high electric field poled guest/host polymers. To maintain a stable dipole alignment, it is a common practice to utilize either high glass transition temperature ($T_g$) polymers with NLO chromophores as side chains or crosslinkable polymers with NLO chromophores that could be locked in the polymer network. However, it is difficult to achieve both large macroscopic nonlinearities and good dipole alignment stability in the same system. This is due to strong intermolecular electrostatic interactions among high dipole moment chromophores and high-temperature aromatic-containing polymers, such as polyimides and polyquinolines that tend to form aggregates. The large void-containing dendritic structures may provide an attractive solution to this critical issue because the dendrons can effectively decrease the interactions among chromophores due to the steric effect. Furthermore, these materials are monodisperse, well-defined, and easily purifiable compared to polymers that are made by the conventional synthetic approaches.

In recent years, organic and material chemists have made significant efforts to further enrich the structure pool of strong electron acceptors, which can be integrated into "push-pull" type of dipolar nonlinear optical chromophores design. The achievements were reflected into more than 250-fold increase in molecular optical nonlinearity based on enhancing the strength of electron acceptor moiety. For example, Dalton, et al. incorporated a unique 2-dicyanomethlyen-3-cyano-4,5,5-trimethyl-2,5-dihydrofuran (TCF) acceptor (see FIG. 1) into a highly efficient ring-locked polyene donor-conjugation system to obtain a series of CLD type of NLO chromophores with exceptionally large molecular nonlinearity (µβ); µβs greater than 18,000×10$^{-48}$ esu (1.9 µm) have been achieved. See, for example, (a) Dalton, L. R., et al., *Mater. Chem.* 9:1905, 1999; and (b) Dalton, L. R., *Opt. Eng.* 39(3):589, 2000.

As described by Melikian et al., the synthesis of TCF involves two steps: 3-methyl-3-hydroxy-2-butanone was condensed with the first molecule of malononitrile to form a cyclized imine intermediate (see FIG. 6 for the structure of the imine), which condensed with a second molecule of malononitrile instantly. Melikian, G.; et al., *Syn. Commun.* 25(19):3045, 1995. Although there are many condensation reactions of heterocyclic imine known in synthetic organic chemistry, the active imine could not be isolated under conventional reaction conditions and often degraded into an inert lactone. In addition, the efforts to react the inert lactone by strong Lewis acid titanium tetrachloride and piperidine have been unsuccessful. As a result, the synthetic methodology used to prepare TCF acceptors is limited to cyanodihydrofuran-type acceptors. However, Liao et al. have recently reported the synthesis and isolation of the active imine using microwave irradiation. Villemin, D. and L. Liao, *Syn. Commun.* 31(11):1771, 2001. The applicability of this imine to the preparation of nonlinear optically active compounds has not been described.

A need exists for novel nonlinear optically active compounds having improved properties including large hyperpolarizability, large dipole moment, and when employed in electro-optic devices, large electro-optic coefficients. There also exists a need for methods for preparing nonlinear optically active compounds having diverse structures and advantageous properties. The present invention seeks to fulfill these needs and provides further related advantages.

SUMMARY OF THE INVENTION

The present invention provides nonlinear optically active compounds, methods for making nonlinear optically active compounds, compounds useful for making nonlinear optically active compounds, methods for making compounds useful for making nonlinear optically active compounds, macrostructures that include nonlinear optically active components, and devices including the nonlinear optically active compounds and the macrostructures.

In one aspect, the invention provides highly polarizable, nonlinear optically active compounds. The compounds generally include three components: a donor moiety covalently coupled to an acceptor moiety through a bridge moiety. In one embodiment, the compound has a π-donor moiety covalently coupled to a π-acceptor moiety through a π-electron conjugated bridge moiety, and the acceptor moiety has the structure:

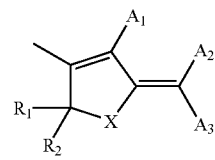

wherein $R_1$ is at least one of an alkyl group, aryl group, or heteroalkyl group; wherein $R_2$ is at least one of an alkyl group, aryl group, or heteroalkyl group; wherein $A_1$ is at least one of an alkyl group, an aryl group, or an electron withdrawing group; wherein $A_2$ is an electron withdrawing group, wherein $A_3$ is an electron withdrawing group; and wherein X is at least one of O, S, or $CH_2$; with the proviso that when X=O or S, $R_1$ and $R_2$ are $CH_3$, and $A_1$ is CN, $A_2$ and $A_3$ are not both CN, with the proviso that when X=O, $R_1$ and $R_2$ are $CH_3$, and $A_1$ is CN, $A_2$ and $A_3$ are not both $SO_2CF_3$, and with the proviso that when X=O, $R_1$ and $R_2$ are $CH_3$, and $A_1$ is $SO_2CF_3$, $A_2$ and $A_3$ are not both $SO_2CF_3$.

In another aspect, the invention provides a method for making a nonlinear optically active compound having a π-donor moiety covalently coupled to a π-acceptor moiety through a π-electron conjugated bridge moiety. In one embodiment, the nonlinear optically active compound is prepared by reacting an appropriately substituted acceptor compound with appropriately substituted donor-bridge compound using focused microwave irradiation.

In a further aspect, the invention provides an acceptor compound that can be reacted with a donor-bridge compound to provide the highly polarizable, nonlinear optical compound. In one embodiment, the compound has the structure:

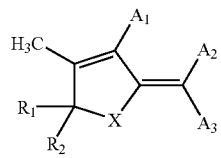

wherein $R_1$ is at least one of an alkyl group, aryl group, or heteroalkyl group; wherein $R_2$ is at least one of an alkyl group, aryl group, or heteroalkyl group; wherein $A_1$ is at least one of an alkyl group, an aryl group, or an electron withdrawing group; wherein $A_2$ is an electron withdrawing group; wherein $A_3$ is an electron withdrawing group; and wherein X is at least one of O, S, or $CH_2$; with the proviso that when X=O or S, $R_1$ and $R_2$ are $CH_3$, and $A_1$ is CN, $A_2$ and $A_3$ are not both CN, with the proviso that when X=O, $R_1$ and $R_2$ are $CH_3$, and $A_1$ is CN, $A_2$ and $A_3$ are not both $SO_2CF_3$, and with the proviso that when X=O, $R_1$ and $R_2$ are $CH_3$, and $A_1$ is $SO_2CF_3$, $A_2$ and $A_3$ are not both $SO_2CF_3$.

The acceptor compound can be prepared by reacting an appropriately substituted imine compound with an appropriately substituted methylene compound using focused microwave irradiation. In one embodiment, the method for making a compound, includes the steps of:
irradiating with microwave irradiation a combination of an imine compound and a methylene compound, wherein the imine compound has the structure:

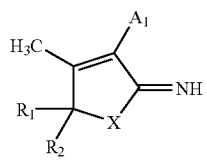

and the methylene compound has the structure:

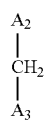

to provide a compound having the structure:

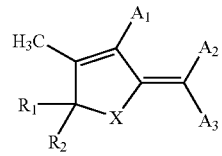

wherein $R_1$ is at least one of an alkyl group, aryl group, or heteroalkyl group; wherein $R_2$ is at least one of an alkyl group, aryl group, or heteroalkyl group; wherein $A_1$ is at least one of an alkyl group, an aryl group, or an electron withdrawing group; wherein $A_2$ is an electron withdrawing group, wherein $A_3$ is an electron withdrawing group; and wherein X is at least one of O, S, or $CH_2$; with the proviso that when X=O, $R_1$ and $R_2$ are $CH_3$, and $A_1$ is CN, $A_2$ and $A_3$ are not both CN.

In a further aspect of the invention, macrostructures that include the nonlinear optically active compounds are provided. In one embodiment, the nonlinear optically active compounds are covalently coupled within the macrostructure.

In other aspects, the invention provides devices that include the nonlinear optically active compounds and devices that include the macrostructures.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION OF THE PREFERRED EMBODIMENT

The present invention provides nonlinear optically active compounds, methods for making nonlinear optically active compounds, compounds useful for making nonlinear optically active compounds, methods for making compounds useful for making nonlinear optically active compounds, macrostructures that include nonlinear optically active compounds, and devices including the nonlinear optically active compounds and the macro structures.

Figure 11:
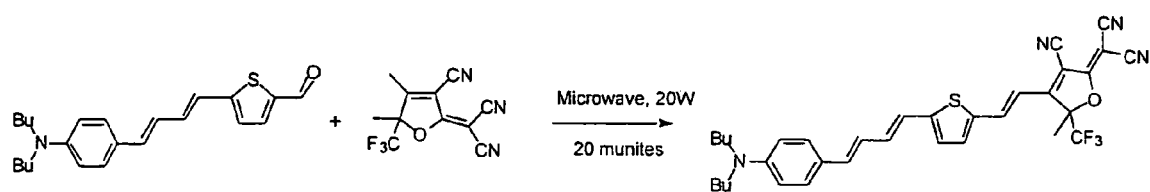
FIG. 11 is a schematic illustration of the preparation of a representative nonlinear optically active compound of the invention.
Figure 13:
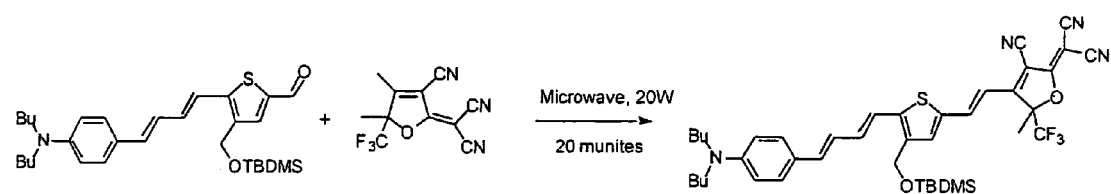
FIG. 13 is a schematic illustration of the preparation of a representative nonlinear optically active compound of the invention.
Figure 16:
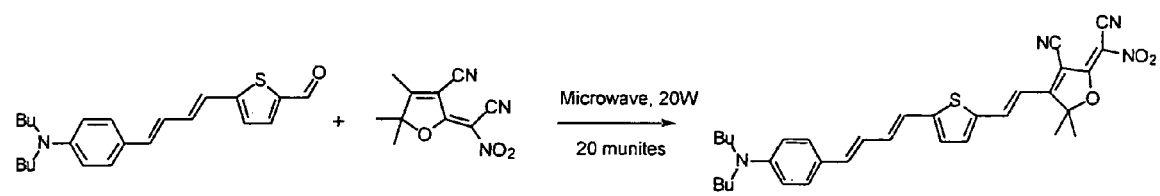
FIG. 16 is a schematic illustration of the preparation of a representative nonlinear optically active compound of the invention.

In one aspect, the invention provides highly polarizable, nonlinear optically active compounds. The compounds generally include three components: a donor moiety covalently coupled to an acceptor moiety through a bridge moiety. For these nonlinear optically active compounds, a π-donor is conjugated to a π-acceptor through a π-electron conjugated bridge. Representative nonlinear optically active compounds of the invention are illustrated in FIGS. 11, 13, and 16.

In another aspect, methods for making the nonlinear optically active compounds are provided. In one embodiment, the nonlinear optically active compound is prepared by reacting an appropriately substituted acceptor compound with appropriately substituted donor-bridge compound using focused microwave irradiation. The preparation of representative nonlinear optically active compounds of the invention by reaction of an appropriately substituted acceptor compound with an appropriately substituted donor-bridge compound is illustrated in FIGS. 11, 13, and 16. Referring to FIGS. 11, 13, and 16, the nonlinear optically active compound is prepared by microwave irradiation of the acceptor and donor-bridge compounds.

Figure 1:
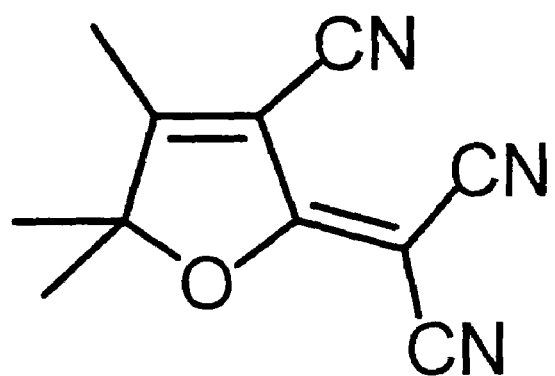
FIG. 1 is the chemical structure of 2-dicyanomethlyen-3-cyano-4,5,5-trimethyl-2,5-dihydrofuran.
Figure 2A:
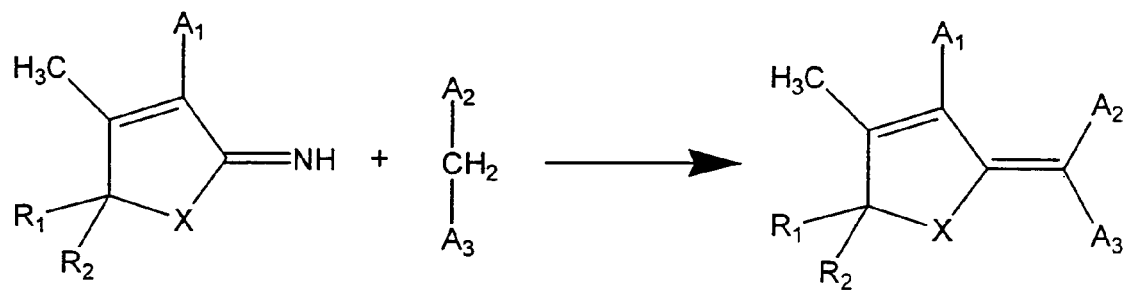
FIG. 2A is a schematic illustration of the preparation of a representative acceptor compound useful in preparing a nonlinear optically active compound of the invention.

In one embodiment, the invention provides an acceptor compound that can be reacted with a donor-bridge compound to provide the highly polarizable, nonlinear optical compound. The acceptor compound can be prepared by reacting an appropriately substituted imine compound with an appropriately substituted methylene compound using microwave irradiation. The reaction of an appropriately substituted imine compound with an appropriately substituted methylene compound is illustrated schematically in FIG. 2A. Referring to FIG. 2A, the acceptor compound is prepared by microwave irradiation of the imine and methylene compounds. As shown in FIG. 2A, the acceptor compound is a 2,5-dihydro five-membered ring compound.

Figure 2B:
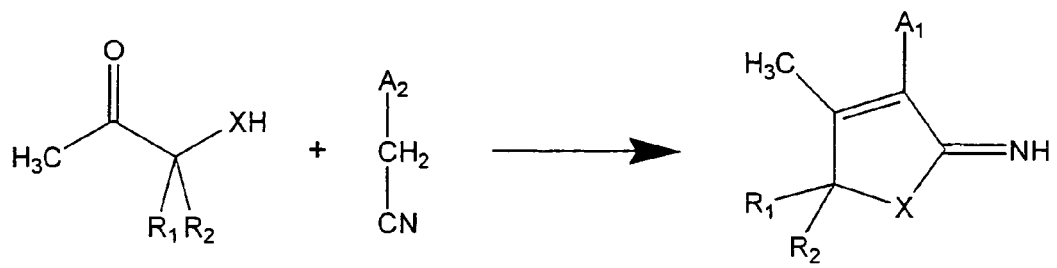
FIG. 2B is a schematic illustration of the preparation of a representative imine compound useful in preparing an acceptor compound and a nonlinear optically active compound of the invention.

Representative imine compounds useful in the invention have the structure shown in FIG. 2A and can be prepared by reaction of an appropriately substituted ketone and an appropriately substituted cyanomethylene compound as shown in FIG. 2B. Reaction of the imine with an appropriately substituted methylene compound provides the acceptor compound.

Figure 2C:
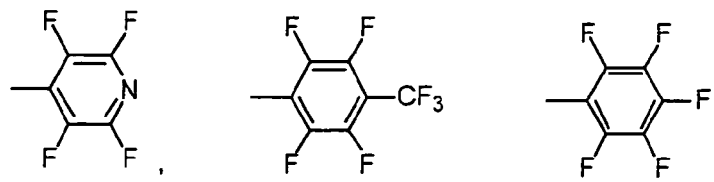
FIG. 2C illustrates the substituents for representative imine compounds, methylene compounds, acceptor compounds, and nonlinear optically active compounds of the invention.
Figure 2C:
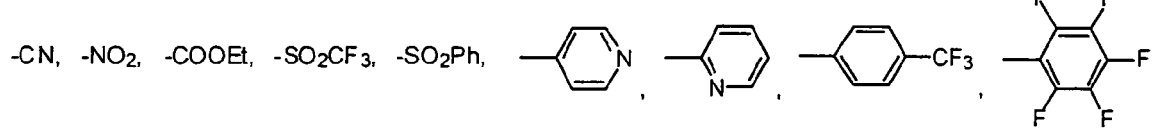
Figure 2C:
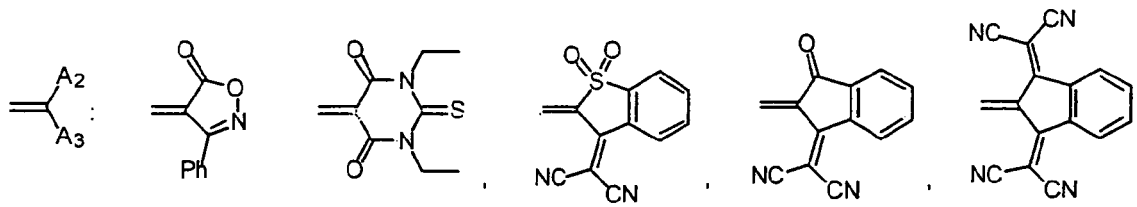

The imine compounds useful in the invention include substituents $R_1$, $R_2$, $A_1$, and X; the methylene compounds useful in the invention include the substituents $A_2$ and $A_3$; the acceptor compounds and the nonlinear optically active compounds of the invention include substituents $R_1$, $R_2$, $A_1$, $A_2$, $A_3$, and X. Representative substituents $R_1$, $R_2$, $A_1$, $A_2$, $A_3$, and X include those shown in FIG. 2C and as described below.

Suitable substituents $R_1$ and $R_2$ include alkyl, aryl, and heteroalkyl substitutents as defined below. Substituents $R_1$ and $R_2$ can also include $CH_3$; $CF_3$; $(CH_2)_nOCH_2OCH_3$, $(CH_2)_nOCOCH_3$, and $(CH_2)_nOSi(CH_3)_2C(CH_3)_3$, where n=3–8; perfluoropyridinyl, perfluorophenyl; and perfluorotoluenyl. Other suitable $R_1$ and $R_2$ substituents include halogenated phenyl substituents, such as 3,4-dichlorophenyl, 2,4-dichlorophenyl, and 2,4-difluorophenyl; and alkyl-substituted phenyl substituents, such as 4-cyclohexyl-4'-phenyl and 4-n-butylphenyl; as described in Mingqian, He, et al., "Synthesis of Chromophores with Extremely High Electro-optic Activity. 1. Thiophene-Bridge-Based Chromophores, *Chem. Mater.* 14(11):4662–4668, 2001. Alternatively, substituents $R_1$ and $R_2$ can be taken together to form a cyclic group to provide a spiro-five-membered ring acceptor group as described in Mingqian, He, et al., "Synthesis of Chromophores with Extremely High Electro-Optic Activity. 1. Thiophene-Bridge-Based Chromophores, *Chem. Mater.* 14(11):4662–4668, 2001. For example, taken together, $R_1$ and $R_2$ can be a cycloalkyl group, such as cyclohexyl group, or a substituted cycloalkyl group, such as fluorenyl group.

Figure 5:
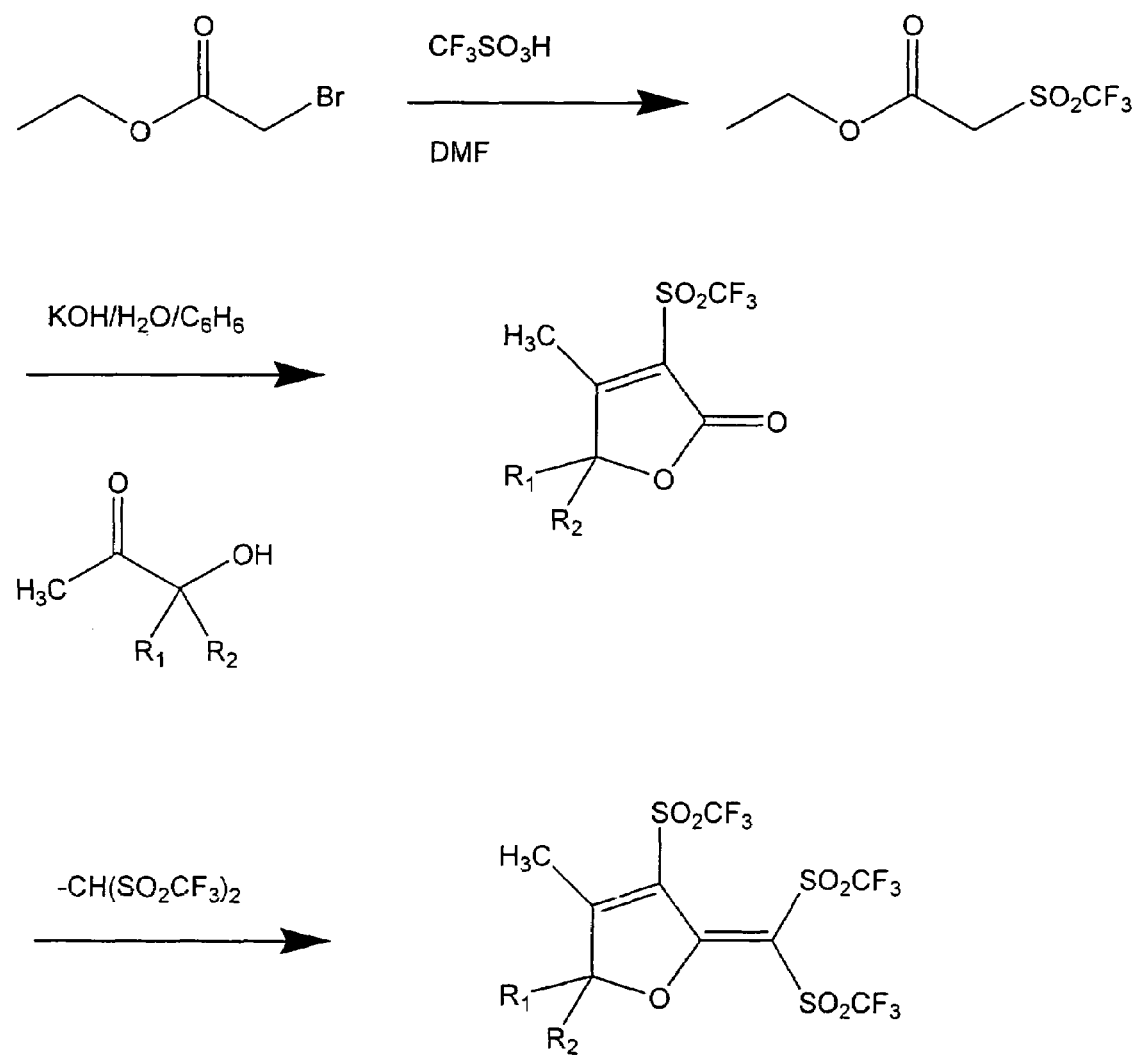
FIG. 5 is a schematic illustration of the preparation of a representative acceptor compound useful in preparing a nonlinear optically active compound of the invention.

Substituents $A_1$, $A_2$, and $A_3$ can be selected from a variety of functional groups. In one embodiment, substituents $A_1$, $A_2$, and $A_3$ are electron-withdrawing groups to fulfill the electron-withdrawing capability of the acceptor moiety within the nonlinear optically active compound. In one embodiment, substituents $A_2$ and $A_3$ are preferably electron-withdrawing groups. In some embodiments, $A_1$ is an alkyl group. Suitable substituents $A_1$, $A_2$, and $A_3$ include those shown in FIG. 2C. The preparation of an acceptor useful in making the nonlinear optically active compounds of the invention is shown in FIG. 5 and described in WO 02/08215 (PCT/US01/23339), incorporated herein by reference in its entirety. Other suitable acceptors are described in WO 02/14305 (PCT/US01/25779), incorporated herein by reference in its entirety.

Substituent X can be oxygen (O), sulfur (S), or methylene ($CH_2$). For X=O and S, the imine compounds (and acceptor compounds) can be prepared from α-hydroxy ketones and α-thioketones, respectively, as shown in FIG. 2B.

2,5-Dihydrofuran compounds (imine and acceptor compounds with X=O) can be readily prepared from α-hydroxy ketones. See, for example, Mingqian, He, et al., "Synthesis of Chromophores with Extremely High Electro-Optic Activity. 1. Thiophene-Bridge-Based Chromophores, *Chem. Mater.*14(11):4662–4668, 2001.

Figure 3A:
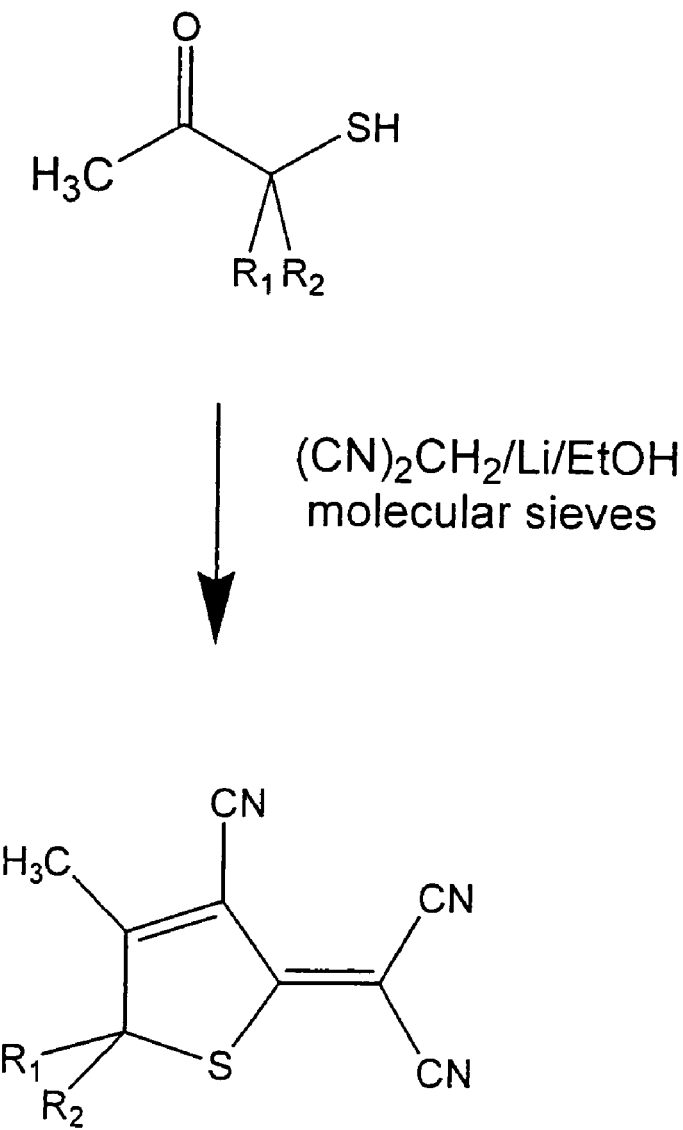
FIG. 3A is a schematic illustration of the preparation of a representative acceptor compound useful in preparing a nonlinear optically active compound of the invention.
Figure 3B:
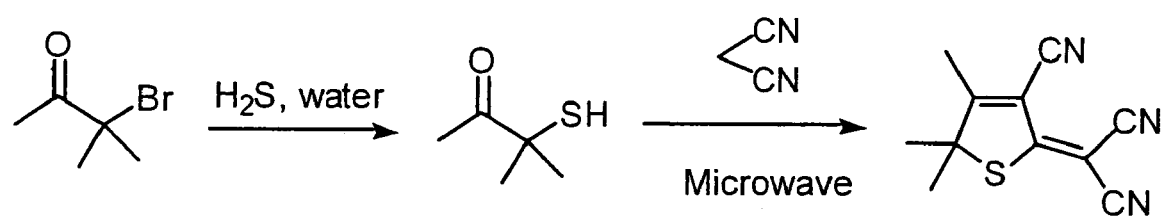
FIG. 3B is a schematic illustration of the preparation of a representative acceptor compound useful in preparing a nonlinear optically active compound of the invention.

The preparation of an S-containing five-membered ring compound from an α-thio methyl ketone by a conventional heating method is described in *Ann.* 602:37, 1957. A preparation of a representative S-containing acceptor compound is shown in FIG. 3A and described in WO 02/14305 (PCT/US01/25779), incorporated herein by reference in its entirety. Alternatively, a representative S-containing acceptor compound can be prepared as shown in FIG. 3B.

Figure 4:
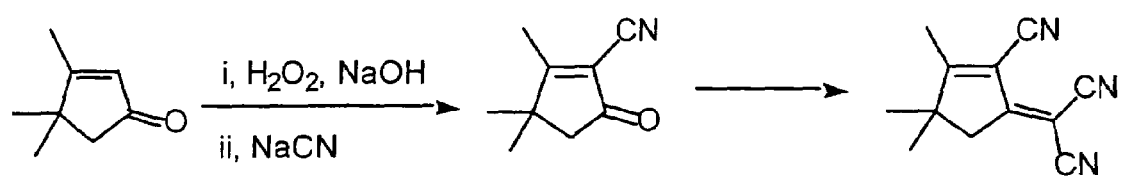
FIG. 4 is a schematic illustration of the preparation of a representative acceptor compound useful in preparing a nonlinear optically active compound of the invention.

Substituent X can also be a methylene ($CH_2$) group. A representative acceptor compound with $X=CH_2$ is shown in FIG. 4.

The acceptor compounds of the invention include a 2-methylene-2,5-dihydro five-membered ring moiety having the structure:

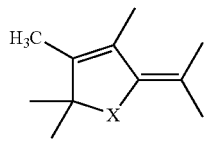

where $X=O$, S, or $CH_2$.

The nonlinear optically active compounds of the invention include a 2-methylene-2,5-dihydro five-membered ring moiety having the structure:

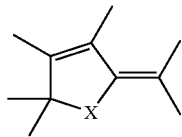

where $X=O$, S, or $CH_2$. In these structure, the positions having bonds without designated substituents can be substituted with a variety of substituents as described herein.

Figure 6:
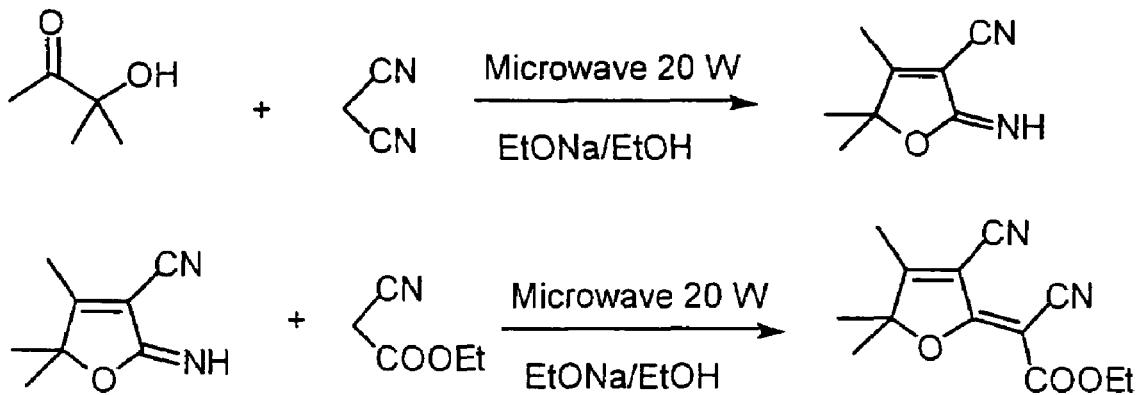
FIG. 6 is a schematic illustration of the preparation of a representative acceptor compound useful in preparing a nonlinear optically active compound of the invention.

The preparation of a representative acceptor from an imine and ethyl cyanoacetate is illustrated in FIG. 6 and described in Example 2.

Figure 7:
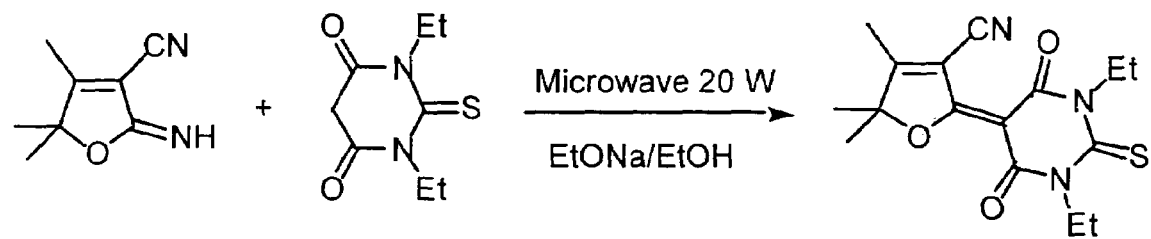
FIG. 7 is a schematic illustration of the preparation of a representative acceptor compound useful in preparing a nonlinear optically active compound of the invention.

The preparation of a representative acceptor from an imine and N,N-diethyl-2-thiobarbituric acid is illustrated in FIG. 7 and described in Example 3.

Figure 8:
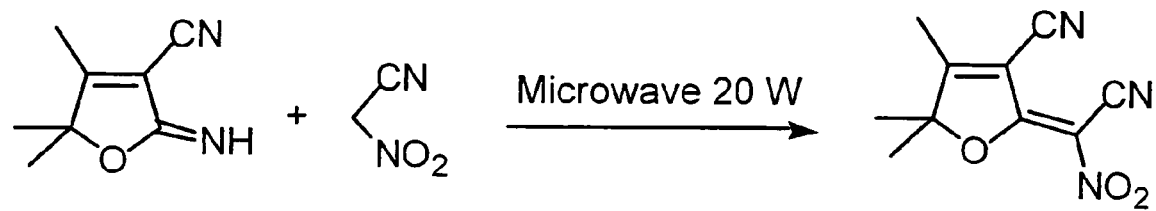
FIG. 8 is a schematic illustration of the preparation of a representative acceptor compound useful in preparing a nonlinear optically active compound of the invention.

The preparation of a representative acceptor from an imine and nitroacetonitrile is illustrated in FIG. 8 and described in Example 4.

Figure 9:
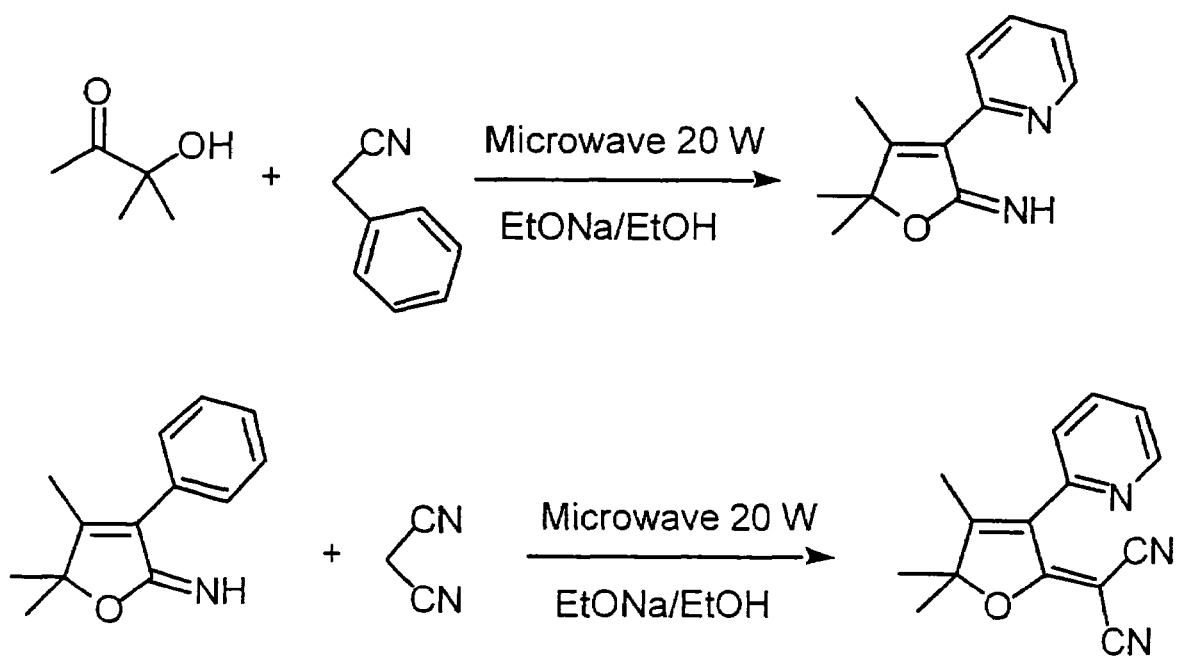
FIG. 9 is a schematic illustration of the preparation of a representative acceptor compound useful in preparing a nonlinear optically active compound of the invention.

The preparation of a representative acceptor from an imine with $A_1$ substituent 2-pyridyl is illustrated in FIG. 9 and described in Example 5.

Figure 10:
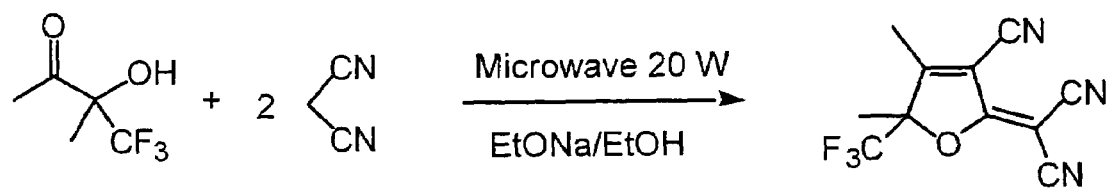
FIG. 10 is a schematic illustration of the preparation of a representative acceptor compound useful in preparing a nonlinear optically active compound of the invention.

The preparation of a representative acceptor from 3-hydroxy-3-trifluoromethyl butan-2-one is illustrated in FIG. 10 and described in Example 6.

The preparation of a representative nonlinear optically active compound is illustrated in FIG. 11 and described in Example 7. The nonlinear optically active compound includes an amino benzene donor moiety and a thiophene bridge moiety.

The preparation of a representative nonlinear optically active compound is illustrated in FIG. 13 and described in Example 8. The nonlinear optically active compound includes an amino benzene donor moiety and a substituted thiophene bridge moiety.

The preparation of a representative nonlinear optically active compound is illustrated in FIG. 16 and described in Example 9. The nonlinear optically active compound includes an amino benzene donor moiety and a thiophene bridge moiety.

The electro-optic properties of representative nonlinear optically active compounds is described in Example 10.

In another aspect, the present invention provides a macromolecular structure that includes one or more nonlinear optically active compounds (i.e., chromophores) that include the acceptor moieties described herein. The macromolecular structure enhances chemical and photochemical stability and maximizes the electro-optic coefficient by preventing intermolecular close approach. For these macromolecular structures, electro-optic coefficient v. chromophore number density curves show steeper slopes than for simple chromophores and with linearity maintained compared to other prior art chromophores. The macromolecular structures can include single or multiple chromophores. The macromolecular structures can be crosslinked.

Representative macromolecular structures include dendrimers and dendritic polymers that incorporate hyperpolarizable chromophores. These dendrimers and dendritic polymers can be based on any of the chromophores described herein.

Chromophore-containing dendrimers can be incorporated into polymers, as discussed below, and used in electro-optic devices. In one embodiment, the dendrimer is incorporated into a polymer host to provide a composite. In another embodiment, the dendrimer is covalently coupled to the polymer host by, for example, crosslinking.

Alternatively, chromophore-containing dendrimers can be used in electro-optic devices directly without a host polymer. In such an embodiment, the dendrimer is crosslinked to form a lattice. Thus, in another embodiment, the invention provides a crosslinkable dendrimer. In this embodiment, the dendrimer is crosslinked to other dendrimers to provide a lattice that does not include a polymer host. The lattice can be derived from crosslinkable dendrimers. The lattice is a polymer-like lattice and can be a hardened lattice.

In another aspect of the invention, chromophore-containing polymers are provided. These polymers can include any one of the chromophores described above, including the chromophore-containing macromolecular structures. In one embodiment, the chromophore is physically incorporated into a polymer to provide a composite. In another embodiment, the chromophore is covalently incorporated into the polymer by, for example, crosslinking. In one embodiment, the chromophore is crosslinked to the polymer in more than one position, for example, a double-ended crosslinked chromophore.

Generally, once a chromophore of appropriate optical nonlinearity (μβ), optical absorption, and stability has been identified, the material is processed into a polymeric material that contains acentrically-aligned chromophores. The process polymeric material can then be translated by, for example, reactive ion etching or photolithography into a waveguide structure that can be integrated with appropriate drive electronics and silica fiber transmission lines. See Dalton, L. et al., "Synthesis and Processing of Improved Organic Second-Order Nonlinear Optical Materials for Applications in Photonics", *Chemistry of Materials* 7(6): 1060–1081, 1995.

To withstand processing conditions and operational conditions (optical power levels at 1.3 and 1.55 microns), chromophore-containing polymers are hardened subsequent to electric field poling to withstand temperatures of 90° C. or greater. As noted above, in certain embodiments, the chromophores include reactive functional groups (e.g., hydroxyl groups) that permit processing into hardened polymer matrices. See Dalton et al. (1995). When thermosetting chemical reactions are employed to lock-in electric field poling-induced acentric order, a stepped poling procedure can be used in which temperature and electric field strength is increased in successive steps to optimize material electrooptic activity. See Kalluri, et al., "Improved Poling and Thermal Stability of Sol-Gel Nonlinear Optical Polymers", Applied Physics Letters 65:2651–2653, 1994. Low loss optical waveguides can be fabricated in polymeric waveguides containing acentrically ordered chromophores. A variety of other techniques can be utilized to fabricate waveguides including, for example, laser ablation, multicolor photolithography, and spatially selective poling.

The chromophores can be incorporated into a variety of host materials including, for example, poly(methylmethacrylate) (PMMA); polyimide; polyamic acid; polystyrene; poly(urethane) (PU); and poly[bisphenol A carbonate-co-4,4'-(3,3,5-trimethylcyclohexylidene)diphenol], amorphous polycarbonate (APC); among others.

In summary, suitable methods for incorporating a chromophore into a polymer include the steps of combining the chromophore with the polymer; electric field poling of the chromophore/polymer mixture to acentrically align chromophores; followed by crosslinking, curing, and hardening the chromophore-containing polymer.

Representative dendrimers and macrostructures related to nonlinear optically active compounds are described in U.S. patent application Ser. No. 10/212,473, filed Aug. 2, 2002, incorporated herein by reference in its entirety.

To better understand the present invention, the following definitions are provided. In general, all technical and scientific terms used herein have the same meaning as commonly understood to one of skill in the art to which this invention belongs, unless clearly indicated otherwise. When an element is cited, all of the element's isotopes are implicitly included (e.g., "hydrogen" stands for hydrogen, deuterium, and tritium). If an isotope is identified explicitly, it is represented by a superscript of the atomic number immediately preceding the symbol (i.e., deuterium is "$^2$H" not "D"). For clarification, listed below are definitions for certain terms used herein to describe embodiments of the present invention. These definitions apply to the terms as they are used throughout this specification, unless otherwise clearly indicated.

As used herein the singular forms "a", "and", and "the" include plural referents unless the context clearly dictates otherwise. For example, "a group" refers to one or more of such groups, while "a chromophore" includes a particular chromophore as well as other family members and equivalents thereof as known to those skilled in the art.

Both substituent groups and molecular moieties are sometimes represented herein with symbols (e.g., R, $R^1$, $\pi$, $\pi^1$, $\pi^2$, D, and A). When the phrase "independently at each occurrence" refers to a symbol, that symbol may represent different actual substituent groups or molecular moieties every time the symbol appears in a formula. For example, the structure below, when described by "wherein R independently at each occurrence is

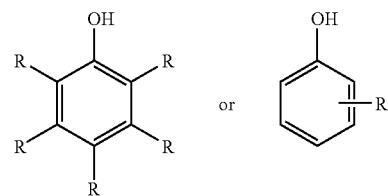

methyl or hydrogen", would correspond to phenol as wells as several methyl substituted phenols including 2-methyl phenol, 3-methyl phenol, 3,4-dimethylphenol, and 2,4,6-trimethylphenol, etc.

"Chromophore" refers to any molecule, aggregate of molecules, or macromolecular structure that absorbs light. Thus, a chromophore can mean a single molecule that absorbs light, an aggregate or macromolecule containing only one absorbing molecule, or an aggregate or macromolecule containing more than one absorbing molecule.

"Electro-optic" (E-O) pertains to altering optical properties of a material by the occurrence of an electric field.

"Electronic" when used to refer to chemical structures and molecules, as opposed to electro-optic devices and components, pertains to electrons in a molecule or on an atom.

"Electric" pertains to electricity and electrical phenomena arising from applied voltages.

"Temporal stability" refers to long-term retention of a particular property. Temporal stability may be affected by any factor that modifies changes in either intermolecular order or intramolecular chemical structure.

A "$\pi$-bridge" or "conjugated bridge" (represented in chemical structures by "$\pi$" or "$\pi^n$" where n is an integer) is comprised of an atom or group of atoms through which electrons can be delocalized from an electron donor (defined below) to an electron acceptor (defined below) through the orbitals of atoms in the bridge. Preferably, the orbitals will be p-orbitals on multiply bonded carbon atoms such as those found in alkenes, alkynes, neutral or charged aromatic rings, and neutral or charged heteroaromatic ring systems. Additionally, the orbitals can be p-orbitals on multiply bonded atoms such as boron or nitrogen or organometallic orbitals. The atoms of the bridge that contain the orbitals through which the electrons are delocalized are referred to here as the "critical atoms." The number of critical atoms in a bridge can be a number from 1 to about 30. The critical atoms can also be substituted further with the following: "alkyl" as defined below, "aryl" as defined below, or "heteroalkyl" as defined below. One or more atoms, with the exception of hydrogen, on alkyl, aryl, or heteroalkyl substituents of critical atoms in the bridge may be bonded to atoms in other alkyl, aryl, or heteroalkyl substituents to form one or more rings.

A "donor" (represented by "D") is an atom or group of atoms with low electron affinity relative to an acceptor (defined below) such that, when the donor is conjugated to an acceptor through a $\pi$ bridge, electron density is transferred from the donor to the acceptor.

An "acceptor" (represented by "A") is an atom or group of atoms with high electron affinity relative to a donor such that, when the acceptor is conjugated to a donor through a $\pi$ bridge, electron density is transferred from the acceptor to the donor.

Representative donors, acceptors, and $\pi$-bridges known to those skilled in the art are described in U.S. Pat. Nos. 6,067,186; 6,090,332; 5,708,178; and 5,290,630.

"Nonlinear" when used in the context of optical phenomenon pertains to second order effects. Such second order, or non-linear, effects typically arise from a "push-pull" chromophore, i.e., a chromophore with the general structure D-π-A.

"Donor coupling" or "π-bridge and/or donor coupling" describe the synthetic chemical step or steps known to those skilled in the art of covalently attaching a chemical group containing a donor to a selected chemical structure. The step maybe divided into multiple steps, wherein the first step covalently attaches a π-bridge that is also reactive and the second step covalently attaches a donor group. Typically, the coupling involves either reacting a π-bridge or donor group containing a carbonyl with a selected chemical structure containing at least one acidic proton or reacting a π-bridge or donor group containing at least one acid proton with a selected chemical structure containing a reactive carbonyl group.

"Acceptor coupling" or "π-bridge and/or acceptor coupling" is the synthetic chemical step or steps known to those skilled in the art of covalently attaching a chemical group containing an acceptor to a selected chemical structure. The step maybe divided into multiple steps, wherein the first step covalently attaches a π-bridge that is also reactive and the second step covalently attaches an acceptor group. Typically, the coupling involves either reacting a π-bridge or acceptor group containing a carbonyl with a selected chemical structure containing at least one acidic proton or reacting π-bridge or acceptor group containing at least one acid proton with a selected chemical structure containing a reactive carbonyl group.

"Dendron" is a branched substituent that has regularly repeating subunits. A dendrimer is a macromolecular structure that contains a core surrounded by one or more dendrons. Often in the art, the terms dendron and dendrimer are used interchangeably.

As used herein, "R" or "R'''" where n is an integer refers to a substituent on an atom. Unless otherwise specifically assigned, —R represents any single atom or any one of the substituent groups defined below. When there is more than one —R in a molecule, the "—R" may independently at each occurrence refer to a single atom or any one of the substituent groups defined below.

The following definitions apply to substituent groups. A given substituent group can have a total number of carbons atoms ranging from 1 to about 200.

"Alkyl" is a saturated or unsaturated, straight or branched, cyclic or multicyclic aliphatic (i.e., non-aromatic) hydrocarbon group containing from 1 to about 30 carbons. Independently the hydrocarbon group, in various embodiments: has zero branches (i.e., is a straight chain), one branch, two branches, or more than two branches; is saturated; is unsaturated (where an unsaturated alkyl group may have one double bond, two double bonds, more than two double bonds, and/or one triple bond, two triple bonds, or more than three triple bonds); is, or includes, a cyclic structure; is acyclic. Exemplary alkyl groups include $C_1$alkyl (i.e., —$CH_3$ (methyl)), $C_2$alkyl (i.e., —$CH_2CH_3$ (ethyl), —CH═$CH_2$ (ethenyl) and —C≡CH (ethynyl)) and $C_3$alkyl (i.e., —$CH_2CH_2CH_3$ (n-propyl), —$CH(CH_3)_2$ (I-propyl), —CH═CH—$CH_3$ (1-propenyl), —C≡C—$CH_3$ (1-propy-nyl), —$CH_2$—CH═$CH_2$ (2-propenyl), —$CH_2$—C≡CH (2-propynyl), —$C(CH_3)$═$CH_2$ (1-methylethenyl), —CH($CH_2$)$_2$ (cyclopropyl), and adamantly. The term "alkyl" also includes groups where at least one of the hydrogens of the hydrocarbon group is substituted with at least one of the following: alkyl; "aryl" as defined below; or "heteroalkyl" as defined below. One or more of the atoms in an alkyl group, with the exception of hydrogen, can be bonded to one or more of the atoms in an adjacent alkyl group, aryl group (aryl as defined below), or heteroalkyl group (heteroalkyl as defined below) to form one or more ring.

"Aryl" is a monocyclic or polycyclic aromatic ring system or a hetereoaromatic ring system containing from 3 to about 30 carbons. The ring system may be monocyclic or fused polycyclic (e.g., bicyclic, tricyclic, etc.). Preferred heteroatoms are nitrogen, oxygen, sulfur, and boron. In various embodiments, the monocyclic aryl ring is C5–C10, or C5–C7, or C5–C6, where these carbon numbers refer to the number of carbon atoms that form the ring system. A C6 ring system, i.e., a phenyl ring, is a preferred aryl group. A C4-S ring system (i.e., a thiophene) is another preferred aryl group. In various embodiments, the polycyclic ring is a bicyclic aryl group, where preferred bicyclic aryl groups are C8–C12, or C9–C10. A naphthyl ring, which has 10 carbon atoms, is a preferred polycyclic aryl group. The term "aryl" also includes groups where at least one of the hydrogens of the aromatic or heteroaromatic ring system is substituted further with at least one of the following: alkyl; halogen; or heteroalkyl (as defined below). One or more of the atoms in an aryl group, with the exception of hydrogen, can be bonded to one or more of the atoms in an adjacent alkyl group, aryl group, or heteroalkyl group (heteroalkyl as defined below) to form one or more rings.

"Heteroalkyl" is an alkyl group (as defined herein) wherein at least one of the carbon atoms or hydrogen atoms is replaced with a heteroatom, with the proviso that at least one carbon atom must remain in the heteroalkyl group after the replacement of carbon or hydrogen with a heteroatom. Preferred heteroatoms are nitrogen, oxygen, sulfur, silicon, and halogen. A heteroatom may, but typically does not, have the same number of valence sites as the carbon or hydrogen atom it replaces. Accordingly, when a carbon is replaced with a heteroatom, the number of hydrogens bonded to the heteroatom may need to be increased or decreased to match the number of valence sites of the heteroatom. For instance, if carbon (valence of four) is replaced with nitrogen (valence of three), then one of the hydrogens formerly attached to the replaced carbon must be deleted. Likewise, if carbon is replaced with halogen (valence of one), then three (i.e., all) of the hydrogens formerly bonded to the replaced carbon must be deleted. Examples of heteroalkyls derived from alkyls by replacement of carbon or hydrogen with heteroatoms is shown immediately below. Exemplary heteroalkyl groups are methoxy (—$OCH_3$), amines (—$CH_2NH_2$), nitriles (—CN), carboxylic acids (—$CO_2H$), other functional groups, and dendrons. The term "heteroalkyl" also includes groups where at least one of the hydrogens of carbon or a heteroatom of the heteroalkyl may be substituted with at least one of the following: alkyl; aryl; and heteroalkyl. One or more of the atoms in a heteroalkyl group, with the exception of hydrogen, can be bonded to one or more of the atoms in an adjacent alkyl group, aryl group, or heteroalkyl group to form one or more rings.

| Alkyl | Heteroalkyl |
|---|---|

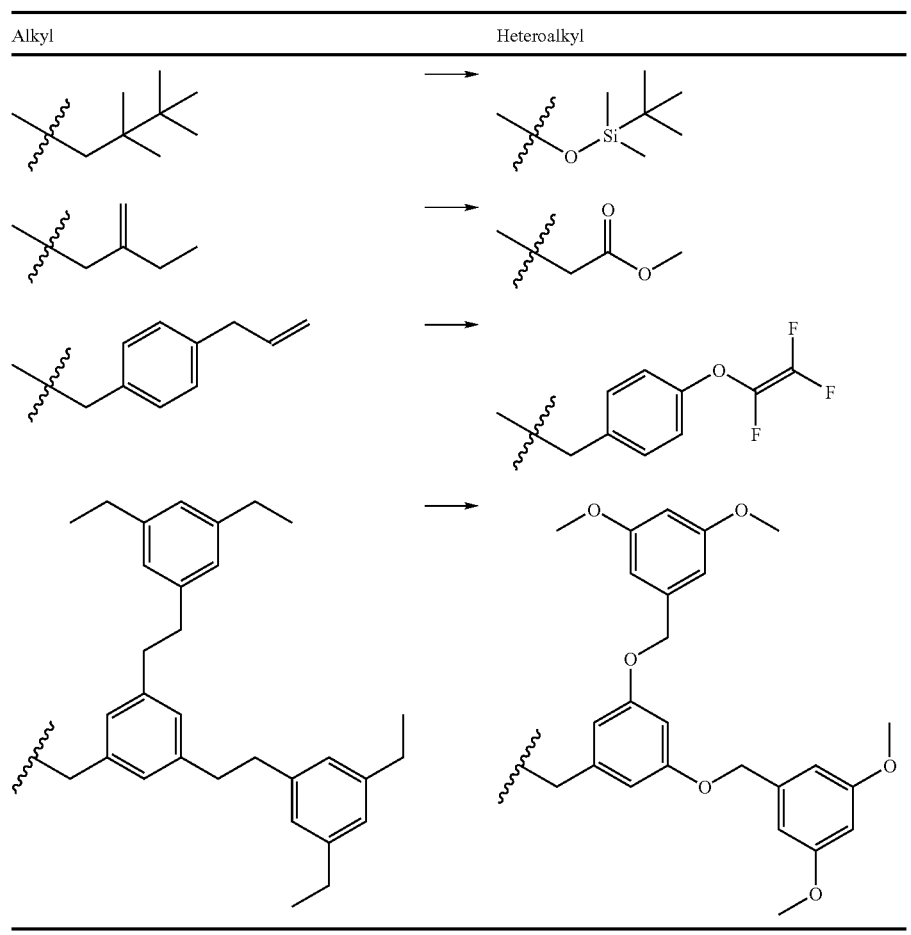

The substituent list that follows is not meant to limit the scope of the definitions above or the inventions described below, but rather merely contains examples of substituents within the definitions above: (1) (alkyl) —$CH_3$, -i-Pr, -n-Bu, -t-Bu, -i-Bu,-$CH_2CH=CH_2$ (allyl) —$CH_2C_6H_5$ (benzyl); (2) (heteroalkyl) —$X_{(0-1)}(CH_2)_{(0-12)}(CF_2)_{(0-12)}(CH_2)_{(0-12)}$ $CH_pZ_q$ (where X includes —O, —S, —$CO_2$— (ester), Z=halogen, p=0–3, q=0–3, and p+q=3) and branched isomers thereof, —$X_{(0-1)}(CH_2)_{(0-12)}(CF_2)_{(0-12)}(CH_2)_{(0-12)}Z$ (where X includes —O, —S, —$CO_2$— (ester), Z includes —OH, —$NH_2$, —$CO_2H$ and esters and amides thereof, —COCl, and —NCO) and branched isomers thereof, —$OCFCF_2$ (TFVE), —$Si(CH_3)_3$ (TMS), —$Si(CH_3)_2$(t-Bu) (TBDMS), —$Si(C_6H_5)$ (TPS), —$Si(C_6F_5)_3$, and dendrons such as illustrated in the dendrimers discussed in Bosman, et al., Chem. Rev. 99:1665–1688, 1957; (3) (aryl) —$C_6H_5$ (phenyl), p-, o-, and/or m-substituted phenyl (with substituents independently selected from —$CH_3$, -i-Pr, -n-Bu, -t-Bu, -i-Bu, —$X_{(0-1)}(CH_2)_{(0-12)}(CF_2)_{(0-12)}(CH_2)_{(0-12)}CH_pZ_q$ (where X includes —O, —S, —$CO_2$— (ester), Z=halogen, p=0–3, q=0–3, and p+q=3) and branched isomers thereof, —$X_{(0-1)}(CH_2)_{(0-12)}(CF_2)_{(0-12)}(CH_2)_{(0-12)}Z$ (where X includes —O, —S, —$CO_2$— (ester), Z includes —OH, —$NH_2$, —$CO_2H$ and esters and amides thereof, -TFVE, —COCl, and —NCO) and branched isomers thereof, —$Si(CH_3)_3$ (TMS), —$Si(CH_3)_2$(t-Bu) (TBDMS), —$CH_2CH=CH_2$ (allyl), and TFVE) and dendrons as illustrated in the dendrimers discussed in Bosman, et al., Chem. Rev. 99:1665, 1999 or U.S. Pat. No. 5,041,516.

The materials and methods described herein can be useful in a variety of electro-optic applications. In addition, these materials and methods may be applied to polymer transistors or other active or passive electronic devices, as well as OLED (organic light emitting diode) or LCD (liquid crystal display) applications.

The use of organic polymers in integrated optics and optical communication systems containing optical fibers and routers has been previously described. The compounds, molecular components, polymers, and compositions (hereinafter, "materials") may be used in place of currently used materials, such as lithium niobate, in most type of integrated optics devices, optical computing applications, and optical communication systems. For instance, the materials may be fabricated into switches, modulators, waveguides, or other electro-optical devices.

For example, in optical communication systems devices fabricated from the compounds of the invention may be incorporated into routers for optical communication systems or waveguides for optical communication systems or for optical switching or computing applications. Because the materials are generally less demanding than currently used materials, devices made from such polymers may be more highly integrated, as described in U.S. Pat. No. 6,049,641, which is incorporated herein by reference. Additionally, such materials may be used in periodically poled applications as well as certain displays, as described in U.S. Pat. No. 5,911,018, which is incorporated herein by reference.

Techniques to prepare components of optical communication systems from optically transmissive materials have been previously described, and may be utilized to prepare such components from materials provided by the present invention. Many articles and patents describe suitable techniques, and reference other articles and patents that describe suitable techniques, where the following articles and patents are exemplary:

Eldada, L. and L. Shacklette, "Advances in Polymer Integrated Optics," *IEEE Journal of Selected Topics in Quantum Electronics* 6(1):54–68 (January/February 2000); Wooten, E. L., et al. "A Review of Lithium Niobate Modulators for Fiber-Optic Communication Systems," *IEEE Journal of Selected Topics in Quantum Electronics* 6 (1): 69–82 (January/February 2000); Heismann, F., et al. "Lithium niobate integrated optics: Selected contemporary devices and system applications," *Optical Fiber Telecommunications III B*, Academic, Kaminow and Koch, eds. New York, 1997, pp. 377–462; Murphy, E., "Photonic switching," *Optical Fiber Telecommunications III B*, Academic, Kaminow and Koch, eds. New York, 1997, pp. 463–501; E. Murphy, *Integrated Optical Circuits and Components: Design and Applications.*, Marcel Dekker, New York, August 1999; Dalton, L., et al., "Polymeric Electro-Optic Modulators: From Chromophore Design to Integration with Semiconductor Very Large Scale Integration Electronics and Silica Fiber Optics," *Ind. Eng. Chem. Res.*38:8–33, 1999; Dalton, L., et al., "From Molecules to Opto-Chips: Organic Electro-Optic Materials," *J. Mater. Chem.*9:1905–1920, 1999; Liakatas, I. et al., "Importance of Intermolecular Interactions in the Nonlinear Optical Properties of Poled Polymers," *Applied Physics Letters* 76:(11): 1368–1370, Mar. 13, 2000; Cai. C., et al., "Donor-Acceptor-Substituted Phenylethenyl Bithiophenes: Highly Efficient and Stable Nonlinear Optical Chromophores," *Organic Letters* 1(11): 1847–1849, 1999; Razna, J., et al., "NLO Properties of Polymeric Langmuir-Blodgett Films of Sulfonamide-Substituted Azobenzenes," *J. of Materials Chemistry* 9: 1693–1698, 1999; Van den Broeck, K., et al., "Synthesis and Nonlinear Optical Properties of High Glass Transition Polyimides," *Macromol. Chem. Phys* 200: 2629–2635, 1999; Jiang, H., and A. K. Kakkar, "Functionalized Siloxane-Linked Polymers for Second-Order Nonlinear Optics," *Macromolecules* 31:2508, 1998; Jen, A. K. -Y. , "High-Performance Polyquinolines with Pendent High-Temperature Chromophores for Second-Order Nonlinear Optics," *Chem. Mater.* 10:471–473, 1998; "Nonlinear Optics of Organic Molecules and Polymers," Hari Singh Nalwa and Seizo Miyata (eds.), CRC Press, 1997; Cheng Zhang, Ph.D. Dissertation, University of Southern California, 1999; Galina Todorova, Ph.D. Dissertation, University of Southern California, 2000; U.S. Pat. Nos. 5,272,218; 5,276,745; 5,286,872; 5,288,816; 5,290,485; 5,290,630; 5,290,824; 5,291,574; 5,298,588; 5,310,918; 5,312,565; 5,322,986; 5,326,661; 5,334,333; 5,338,481; 5,352,566; 5,354,511; 5,359,072; 5,360,582; 5,371,173; 5,371,817; 5,374,734; 5,381,507; 5,383,050; 5,384,378; 5,384,883; 5,387,629; 5,395,556; 5,397,508; 5,397,642; 5,399,664; 5,403,936; 5,405,926; 5,406,406; 5,408,009; 5,410,630; 5,414,791; 5,418,871; 5,420,172; 5,443,895; 5,434,699; 5,442,089; 5,443,758; 5,445,854; 5,447,662; 5,460,907; 5,465,310; 5,466,397; 5,467,421; 5,483,005; 5,484,550; 5,484,821; 5,500,156; 5,501,821; 5,507,974; 5,514,799; 5,514,807; 5,517,350; 5,520,968; 5,521,277; 5,526,450; 5,532,320; 5,534,201; 5,534,613; 5,535,048; 5,536,866; 5,547,705; 5,547,763; 5,557,699; 5,561,733; 5,578,251; 5,588,083; 5,594,075; 5,604,038; 5,604,292; 5,605,726; 5,612,387; 5,622,654; 5,633,337; 5,637,717; 5,649,045; 5,663,308; 5,670,090; 5,670,091; 5,670,603; 5,676,884; 5,679,763; 5,688,906; 5,693,744; 5,707,544; 5,714,304; 5,718,845; 5,726,317; 5,729,641; 5,736,592; 5,738,806; 5,741,442; 5,745,613; 5,746,949; 5,759,447; 5,764,820; 5,770,121; 5,76,374; 5,776,375; 5,777,089; 5,783,306; 5,783,649; 5,800,733; 5,804,101; 5,807,974; 5,811,507; 5,830,988; 5,831,259; 5,834,100; 5,834,575; 5,837,783; 5,844,052; 5,847,032; 5,851,424; 5,851,427; 5,856,384; 5,861,976; 5,862,276; 5,872,882; 5,881,083; 5,882,785; 5,883,259; 5,889,131; 5,892,857; 5,901,259; 5,903,330; 5,908,916; 5,930,017; 5,930,412; 5,935,491; 5,937,115; 5,937,341; 5,940,417; 5,943,154; 5,943,464; 5,948,322; 5,948,915; 5,949,943; 5,953,469; 5,959,159; 5,959,756; 5,962,658; 5,963,683; 5,966,233; 5,970,185; 5,970,186; 5,982,958; 5,982,961; 5,985,084; 5,987,202; 5,993,700; 6,001,958; 6,005,058; 6,005,707; 6,013,748; 6,017,470; 6,020,457; 6,022,671; 6,025,453; 6,026,205; 6,033,773; 6,033,774; 6,037,105; 6,041,157; 6,045,888; 6,047,095; 6,048,928; 6,051,722; 6,061,481; 6,061,487; 6,067,186; 6,072,920; 6,081,632; 6,081,634; 6,081,794; 6,086,794; 6,090,322; and 6,091,879.

The foregoing references provide instruction and guidance to fabricate waveguides from materials generally of the types described herein using approaches such as direct photolithography, reactive ion etching, excimer laser ablation, molding, conventional mask photolithography, ablative laser writing, or embossing (e.g., soft embossing). The foregoing references also disclose electron donors and electron bridges that may be incorporated into the compounds of the invention or that may also incorporate an electron donor and/or electron bridges described herein.

Components of optical communication systems that may be fabricated, in whole or part, with materials according to the present invention include, without limitation, straight waveguides, bends, single-mode splitters, couplers (including directional couplers, MMI couplers, star couplers), routers, filters (including wavelength filters), switches, modulators (optical and electro-optical, e.g., birefringent modulator, the Mach-Zender interferometer, and directional and evanescent coupler), arrays (including long, high-density waveguide arrays), optical interconnects, optochips, single-mode DWDM components, and gratings. The materials described herein may be used with, for example, wafer-level processing, as applied in, for example, vertical cavity surface emitting laser (VCSEL) and CMOS technologies.

In many applications, the materials described herein may be used in lieu of lithium niobate, gallium arsenide, and other inorganic materials that currently find use as light-transmissive materials in optical communication systems.

The materials described herein may be used in telecommunication, data communication, signal processing, information processing, and radar system devices and thus may be used in communication methods relying, at least in part, on the optical transmission of information. Thus, a method according to the present invention may include communicating by transmitting information with light, where the light is transmitted at least in part through a material including a compound of the invention or related macrostructure.

The materials of the present invention can be incorporated into various electro-optical devices. Accordingly, in another aspect, the invention provides electro-optic devices including the following.

An electro-optical device comprising a compound or related macrostructure according to the present invention;

A waveguide comprising a compound or related macrostructure according to the present invention;

An optical switch comprising a compound or related macrostructure according to the present invention;

An optical modulator comprising a compound or related macrostructure according to the present invention;

An optical coupler comprising a compound or related macrostructure according to the present invention;

An optical router comprising a compound or related macrostructure according to the present invention;

A communications system comprising a compound or related macrostructure according to the present invention;

A method of data transmission comprising transmitting light through or via a compound or related macrostructure according to the present invention;

A method of telecommunication comprising transmitting light through or via a compound or related macrostructure according to the present invention;

A method of transmitting light comprising directing light through or via a compound or related macrostructure according to the present invention;

A method of routing light through an optical system comprising transmitting light through or via a compound or related macrostructure according to the present invention;

An interferometric optical modulator or switch, comprising: (1) an input waveguide; (2) an output waveguide; (3) a first leg having a first end and a second end, the first leg being coupled to the input waveguide at the first end and to the output waveguide at the second end; and 4) and a second leg having a first end and a second end, the second leg being coupled to the input waveguide at the first end and to the output waveguide at the second end, wherein at least one of the first and second legs includes a compound or related macrostructure according to the present invention;

An optical modulator or switch, comprising: (1) an input; (2) an output; (3) a first waveguide extending between the input and output; and (4) a second waveguide aligned to the first waveguide and positioned for evanescent coupling to the first waveguide; wherein at least one of the first and second legs includes a compound or related macrostructure according to the present invention. The modulator or switch may further including an electrode positioned to produce an electric field across the first or second waveguide;

An optical router comprising a plurality of switches, wherein each switch includes: (1) an input; (2) an output; (3) a first waveguide extending between the input and output; and (4) a second waveguide aligned to the first waveguide and positioned for evanescent coupling to the first waveguide; wherein at least one of the first and second legs includes a compound or related macrostructure according to the present invention. The plurality of switches may optionally be arranged in an array of rows and columns.

The highly polarizable, nonlinear optically active compounds of the invention include a donor moiety covalently coupled to an acceptor moiety through a bridge moiety. The acceptor moiety can be incorporated into the compound by reacting an appropriately substituted acceptor compound with an appropriately substituted donor-bridge compound. In one aspect, the invention provides acceptor compounds that are 2,5-dihydro five-member heterocyclic compounds. In one embodiment, the acceptor compound is prepared by reacting an activated imine precursor with a methylene compound under focused single mode microwave irradiation. By selective derivatization of the imine precursor and methylene compound, the electron-withdrawing ability in the resulting 2,5-dihydro five-member heterocyclic compound can be controlled. A nonlinear optically active compound having an acceptor moiety derived from the acceptor compound permits the optimization of molecular hyperpolarizability, absorption at near-IR region, and thermal, chemical and photochemical stabilities of the resulting nonlinear optical compound. The functional groups of the acceptor compounds can be widely varied to permit the ready covalent coupling to benzenoid aromatic, heterocyclic aromatic, and polyene bridges and to permit covalent coupling with polymers to provide crosslinkable and dendritic nonlinear optically active polymer systems.

The following examples are provided for the purpose of illustrating, not limiting, the invention.

EXAMPLES

Example 1

Representative Method for Microwave Synthesis

In this example, a representative method for microwave assisted synthesis and microwave system for the synthesis is described.

A microwave-based synthesis system useful in making the acceptor compounds and nonlinear optically active compounds of the invention is a laboratory system for the process control, analytical and life sciences markets commercially available under the designation Discover System (CEM Corporation, Matthews, N.C.). The system is designed for industrial use in synthetic laboratories. This system bridges the gap between functionality and economy. The system uses a manually accessed single-mode reaction chamber, which assures that the sample is always in a homogenous, highly dense microwave field (i.e., the system "focuses" the field onto the reaction components).

The system can be operated at atmospheric conditions using "open" vessels or at elevated pressure and temperature, using "sealed" vessels. Operating at atmospheric conditions, the system can accommodate vessels ranging in volumes of 5 mL up to 125 mL. Operating at elevated pressures, the system can accommodate a 10 mL vessel that is sealed with a septum. The features include a "self tuning" single-mode microwave cavity design to provide maximum coupling of the delivered microwave energy and the sample load. The system is independent of the sample volume, vessel geometry, and the sample temperature. The system includes temperature feedback control, pressure feedback control (for closed systems), in situ reaction stirring, operation under an inert atmosphere, in situ reaction cooling, and true microwave energy continuous tenability.

Microwave chemistry takes advantage of the physical properties of chemical entities to "couple" or accept the transfer of this highly intense energy source instantaneously to produce accelerated reaction rates (10–1,000 times faster than thermally driven reactions). Because of the nature of the microwave absorption, it is possible to target or "focus"

the direct energy transfer in reaction schemes. As the transfer of microwave energy is immediate, there is no residual energy transfer after the source is turned off, as there is with thermal heating, which means cleaner chemistry with less post reaction work-up. As a result, microwave-enhanced synthesis reactions typically produce yield increases of 10–30% over thermally driven reactions, offering superior selectivity and the opportunity to practice synthetic chemistry in an accelerated manner. Because microwave energy transfers directly to the reactants, there is no need to use bulk solvent for heat transfer agents, thereby minimizing or eliminating the need to use potentially hazardous reagents.

Example 2

Preparation of a Representative Acceptor 2-(1'-Ethoxycarbonyl-1'-cyano)vinyl-3-cyano-4,5,5-trimethyl-2,5-dihydrofuran In this example, the preparation of a representative acceptor, 2-(1'-ethoxycarbonyl-1'-cyano)vinyl-3-cyano-4,5,5-trimethyl-2,5-dihydrofuran, is described. The preparation is illustrated schematically in FIG. 6.

2-Imino-3-cyano-4,5,5-trimethyl-2,5-dihydrofuran. A mixture of 3-hydroxy-3-methylbutan-2-one (3 mmol, 306 mg), malononitrile (3 mmol, 198 mg) and sodium ethoxide (0.3 mmol), prepared from sodium (0.3 mmol, 6.9 mg), in ethanol (0.3 mL) was irradiated under focused microwave at 20 W for 8 minutes. Solvent was removed by rotary evaporation and the residue was purified via a flash chromatography on silica gel with a gradient eluent of dichloromethane to 2% ethanol in dichloromethane to afford 200 mg of product as a pale solid (44%). $^1$H NMR (CDCl$_3$) δ 7.06 (br, 1H), 2.18 (s, 1H). 1.45 (s, 1H).

2-(1'-Ethoxycarbonyl-1'-cyano)methylene-3-cyano-4,5,5-trimethyl-2,5-dihydrofuran. To a mixture of 2-imino-3-cyano-4,5,5-trimethyl-2,5-dihydrofuran (0.5 mmol, 75 mg) and ethyl cyanoacetate (0.6 mmol, 68 mg) in ethanol (1 mL) was added sodium (0.1 mmol, 2.3 mg). After sodium was completely dissolved in the solution, the mixture was irradiated under focused microwave at 20 W for 8 minutes. Solvent was removed by rotary evaporation and the residue was purified via a flash chromatography on silica gel with a gradient eluent of dichloromethane to 0.25% ethanol in dichloromethane to afford 72 mg of product as a white solid (58%). $^1$H NMR (CDCl$_3$) δ 4.31 (q, 7.0 Hz, 2H), 2.33 (s, 3H), 1.56 (s, 6H), 1.33 (t, 7.0 Hz, 3H).

Example 3

Preparation of a Representative Acceptor 5-(3-Cyano-4 5,5-trimethyl-2,5-dihydro-2-furanyl)-1,3,-diethyl-2-thiobarbituric acid In this example, the preparation of a representative acceptor, 5-(3-cyano-4,5,5-trimethyl-2,5-dihydro-2-furanyl)-1,3-diethyl-2-thiobarbituric acid, is described. The preparation is illustrated schematically in FIG. 7.

To a mixture of 2-imino-3-cyano-4,5,5-trimethyl-2,5-dihydrofuran (0.5 mmol, 75 mg) and 1,3-diethyl-2-thiobarbituric acid (0.5 mmol, 100 mg) in ethanol (1 mL) was added sodium (0.1 mmol, 2.3 mg). After sodium was completely dissolved in the solution, the mixture was irradiated under focused microwave at 20 W for 8 minutes and 35 W for 8 minutes. Solvent was removed by rotary evaporation and the residue was purified via a flash chromatography on silica gel with a gradient eluent of dichloromethane to 2% ethanol in dichloromethane to afford 17 mg of product as a brown solid (10%). $^1$H NMR (CDCl$_3$) δ 4.55 (q, 7.0 Hz, 4H), 2.41 (s, 3H), 1.64 (s, 6H), 1.28 (t, 6.4 Hz, 6H).

Example 4

Preparation of a Representative Acceptor 2-(1'-Cyano-1'-nitro)methylene-3-cyano-4,5,5-trimethyl-2,5-dihydrofuran In this example, the preparation of a representative acceptor, 2-(1'-cyano-1'-nitro)methylene-3-cyano-4,5,5-trimethyl-2,5-dihydrofuran, is described. The preparation is illustrated schematically in FIG. 8.

A mixture of 2-imino-3-cyano-4,5,5-trimethyl-2,5-dihydrofuran (1.84 mmol, 276 mg) and nitroacetonitrile (3.66 mmol, 315 mg) in a mixture of ethanol (0.5 mL), diethyl ether (5 mL) and methylene chloride (0.5 mL) was irradiated under focused microwaves 20 W for 4 minutes. Solvent was removed by rotary evaporation and the residue was purified via a flash chromatography on silica gel with an eluent of 1% ethanol in dichloromethane to afford 165 mg of product as a yellow solid (41%). $^1$H NMR (CDCl$_3$) δ 2.54 (s, 3H), 1.78 (s, 3H), 1.77 (s, 3H).

Example 5

Preparation of a Representative Acceptor

2-Dicyanomethylene-3-(2'-pyridyl)-4,5,5-trimethyl-2,5-dihydrofuran

In this example, the preparation of a representative acceptor, 2-dicyanomethylene-3-(2'-pyridyl)-4,5,5-trimethyl-2,5-dihydrofuran, is described. The preparation is illustrated schematically in FIG. 9.

2-Imino-3-(2'-pyridyl)-4,5,5-trimethyl-2,5-dihydrofuran. A mixture of 3-hydroxy-3-methylbutan-2-one (3 mmol, 306 mg), 2-pyridylacetonitrile (3 mmol, 355 mg) and sodium ethoxide (0.3 mmol), prepared from sodium (0.3 mmol, 6.9 mg), in ethanol (0.3 mL) was irradiated under focused microwave at 20 W for 8 minutes. Solvent was removed by rotary evaporation and the residue was purified via a flash chromatography on silica gel with a gradient eluent of dichloromethane to 1% ethanol in dichloromethane to afford 606 mg of product as a brown oil at almost quantitative yield. $^1$H NMR (CDCl$_3$) δ 8.63–8.67 (m, 1H), 7.71–7.75 (m, 2H), 7.18–7.26 (m, 1H), 2.14 (s, 3H), 1.47 (s, 6H).

2-Dicyanomethylene-3-(2'-pyridyl)-4,5,5-trimethyl-2,5-dihydrofuran. To a mixture of 2-imino-3-(2'-pyridyl)-4,5,5-trimethyl-2,5-dihydrofuran (1.5 mmol, 303 mg) and malononitrile (1.5 mmol, 99 mg) in ethanol (0.1 mL) was added sodium (0.15 mmol, 3.5 mg). After sodium was completely dissolved in the solution, the mixture was irradiated under focused microwave at 20 W for 8 minutes. Solvent was removed by rotary evaporation and the residue was purified via a flash chromatography on silica gel with a gradient eluent of dichloromethane to 2% ethanol in dichloromethane to afford 296 mg of product as a brown solid (79%). $^1$H NMR (CDCl$_3$) δ 8.71–8.75 (m, 1H), 7.76–7.85 (m, 1H), 7.24–7.42 (m, 2H), 1.97 (s, 3H), 1.62 (s, 6H).

Example 6

Preparation of a Representative Acceptor

2-Dicyanomethylene-3-cyano-4,5-dimethyl-5-trifluoromethyl-2,5-dihydrofuran

In this example, the preparation of a representative acceptor, 2-dicyanomethylene-3-cyano-4,5-dimethyl-5-trifluoromethyl-2,5-dihydrofuran, is described. The preparation is illustrated schematically in FIG. 10.

A mixture of 3-hydroxy-3-methylbutan-2-one (3 mmol, 470 mg), malononitrile (6 mmol, 396 mg) and sodium ethoxide (0.45 mmol), in situ, prepared from sodium (0.45 mmol, 10.4 mg), in ethanol (0.45 mL) was irradiated under focused microwave at 20 W for 20 minutes. Solvent was removed by rotary evaporation and the residue was purified via a flash chromatography on silica gel with a gradient eluent of dichloromethane to 2% ethanol in dichloromethane to afford 418 mg of product as a pale yellow solid (55%). $^1$H NMR (CDCl$_3$) δ 2.44 (s, 3H), 1.83 (s, 3H).

Example 7

Preparation of a Representative Nonlinear Optically Active Compound Amino Benzene Donor; Thiophene Bridge; Tricyanodihydrofuran Acceptor In this example, the preparation of a representative nonlinear optically active compound is described. The compound includes an amino benzene donor, thiophene bridge, and tricyanodihydrofuran acceptor having a trifluoromethyl substituent. The preparation is illustrated schematically in FIG. 11.

A mixture of N,N-dibutyl-4-[(1E,3E)-4-(5-formylthien-2-yl)-1,3-butadienyl]aniline (757 mg, 2.06 mmol), prepared as described below, and 2-dicyanomethylene-3-cyano-4,5-dimethyl-5-trifluoromethyl-2,5-dihydrofuran 7 (522 mg, 2.06 mmol) in 3 mL of ethanol was heated under microwave radiation at 20 W for 20 minutes. The resulting mixture was concentrated and purified through a flash chromatography on silica gel with a gradient eluent of hexanes/ethyl acetate (20/1–3/1) to give 530 mg of product as dark solid (43%). $^1$H NMR (CDCl$_3$) δ 8.11 (d, 15 Hz, 1H), 7.42 (d, 3.8 Hz, 1H), 7.32 (d, 9.2 Hz, 2H), 7.01 (d, 4 Hz, 1H), 6.9–7.1 (m, 1H), 6.65–6.75 (m, 3H), 6.59 (d, 9.0 Hz, 2H), 6.46 (d, 15.4 Hz, 1H), 3.29 (t, 7.6 Hz, 4H), 1.89 (s, 3H), 1.57 (quin, 8.8 Hz, 4H), 1.35 (sexi, 6.8 Hz, 4H), 0.95 (t, 7.2 Hz, 6H).

Figure 12:
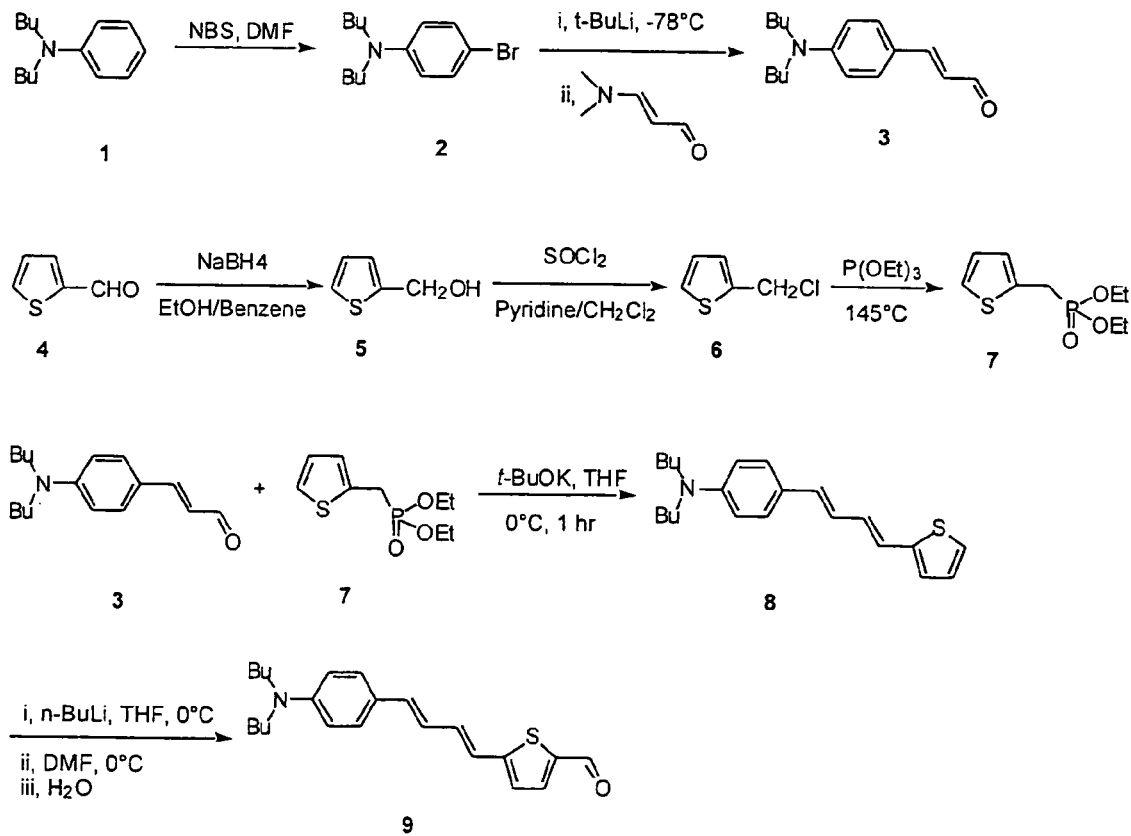
FIG. 12 is a schematic illustration of the preparation of a donor-bridge compound useful in preparing a representative nonlinear optically active compound of the invention.

N,N-dibutyl-4-[(1E,3E)-4-(5-formylthien-2-yl)-1,3-butadienyl]aniline. As shown FIG. 12, regioselective bromination on N,N-dibutylaniline 1 at para-position generated bromoaniline 2 by NBS (N-bromosuccinimide) at almost quantitative yields. Without further purification, the resulting bromoaniline 2 was treated with t-BuLi at −78° C. and quenched with 3-(dimethylamino)acrolein to afford 3-(N,N-dibutylaminophenyl)-acrolein 3 in 60% yield. Synthesis of conjugation bridge building block, diethyl (thien-1-yl)-methylphosphonate 7, was started from commercially available 2-thiophenecarboxaldehyde, after a NaBH$_4$ reduction followed by the treatment with thionyl chloride, the resulting 2-chloromethylthiophene 6 was reacted with triethyl phosphate to afford diethyl (thien-1-yl)-methylphosphonate 7. Exclusive E-configuration alkene N,N-dibutyl-4-[(1E,3E)-4-(thien-2-yl)-1,3-butadienyl]-aniline 8 was obtained from a Wittig-Horner-Emmons condensation of 3-(N,N-dibutylaminophenyl)acrolein 3 and diethyl (thien-1-yl)-methylphosphonate 7.

4-Bromo-N,N-dibutylaniline (2). To a stirred solution of N,N-dibutylaniline 1 (35.2 g, 172 mmol) in 50 mL of DMF was added N-bromosuccinimide (32.09 g, 180 mmol) in 85 mL of DMF dropwise at room temperature. The mixture was stirred overnight at room temperature to afford a dark green solution. The solution was poured into 200 mL of water with crushed ice and extracted with 3×120 ml of hexane. After washed with 100 mL of saturated brine, the combined organic layers were dried over Na$_2$SO$_4$ and concentrated to afford 46.7 g of 2 (95%) as pale yellow oils, which were used in the subsequent reaction without further purification. $^1$H NMR (CDCl$_3$) δ 7.26 (d, 9.1 Hz, 2H), 6.52 (d, 9.1 Hz, 2H), 3.24 (t, 7.4 Hz, 4H), 1.55 (quin, 7.3 Hz, 4H), 1.35 (sexi, 7.7 Hz, 4H), 0.96 (t, 7.4 Hz, 6H).

3-(N,N-Dibutylaminophenyl)acrolein (3). A stirred solution of 4-bromo-N,N-dibutylaniline 2 (32.4 g, 113.8 mmol) in 200 mL of THF was cooled to −78° C. 147 mL of t-butyl lithium (1.7 M, 250 mmol) was added dropwise and the resulting dark mixture was stirred for 1 hour at −78° C. A solution of 3-(dimethylamino)acrolein (16.9 g, 171 mmol) in 50 mL of THF was added into the mixture slowly. After this addition, the reaction mixture was stirred at −78° C. for additional 2 hours, warmed up to room temperature and stirred for another 2 hours to allow the completion of reaction. The resulting mixture was quenched with 8 mL of water and stirred overnight. THF was removed via rotary evaporation. The residue was taken by 500 mL of water and extracted with 3x300 mL of dichloromethane. The combined organic layers were dried over Na$_2$SO$_4$ and concentrated. The crude product was purified via a flash chromatography on silica gel with 10% ethyl acetate in hexanes to afford 16.2 g product as orange oil (60%). $^1$H NMR (CDCl$_3$) δ 9.55 (d, 5.6 Hz, 1H), 7.40 (d, 9 Hz, 2H), 7.34 (d, 15.3 Hz, 1H), 6.6 (d, 8.4 Hz, 2H), 6.49 (dd, 15 Hz, 10 Hz, 1H), 3.30 (t, 8.1 Hz, 4H), 1.5–1.6 (m, 4H), 1.35 (sexi, 7.8 Hz, 4H), 0.95 (t, 7.2 Hz, 6H).

2-Thiophenemethanol (5). To a solution of 2-thiophenecarboxaldehyde 4 (56.1 g, 0.5 mol) in a co-solvent of 200 mL ethanol and 200 mL of benzene was added sodium borohydride (22.70 g, 0.6 mol) in portions at 0° C. with caution. Upon the cease of violent bubble eruption, ice-water bath was removed and the mixture was raised to room temperature and stirred for another two hours. The white solid was filtered through Buchner funnel and the resulting solution was concentrated and dried over K$_2$CO$_3$ overnight to afford 52.5 g of 2-thiophenemethanol as clear oil (92%). The crude product was used in the subsequent reaction without further purification. $^1$H NMR (CDCl$_3$) δ 7.27 (dd, J=4.8, 1.4 Hz, 1H), 6.94–7.02 (m, 2H), 4.82 (s, 2H), 1.77 (br, 1H).

2-Chloromethylthiophene (6). To a solution of 2-thiophenemethanol 5 (58 g, 509 mmol) and pyridine (60 g, 763 mmol) in 600 mL of dry CH2Cl2 was added thionyl chloride dropwise at 0° C. and stirred for 1 hour, the resulting solution was stirred at room temperature over night and was taken by 500 mL of water. The organic layer was separated and the aqueous layer was extracted by 300 mL×2 CH$_2$Cl$_2$. The organic layers were combined and washed by 600 mL of 5% NaHCO$_3$ aq., 300 mL of brine, dried over Na$_2$SO$_4$ and concentrated to afford 40 g of 6 as oil (60%). The crude product was used in the subsequent reaction without further purification and was stored over MgSO$_4$ before use. $^1$H NMR (CDCl$_3$) δ 7.30 (dd, J=5.0, 0.8 Hz, 1H), 7.05–7.08 (m, 1H), 6.94 (dd, J=5.1, 3.4 Hz, 1H), 4.80 (s, J=0.6 Hz, 2H).

Diethyl 2-thienylmethylphosphonate (7). A mixture of 2-chloromethylthiophene 6 (183.6 g, 1385 mmol) and triethyl phosphate (241.5 g, 1454 mmol) was heated at 140–145° C. for 3 hours, the resulting liquid was cooled to 120 ° C. before nitrogen bubble was blown underneath the surface for 1.5 hours. The liquid was cooled to room temperature to afford 324 g of product and was used in the subsequent reaction without further purification (99%). $^1$H NMR (CDCl$_3$) δ 7.38 (dd, J=4.8, 0.8 Hz, 1H), 7.14–7.18 (m, 1H), 6.90–7.00 (m, J=5.1, 1H), 4.03 (q, J=7.3 Hz, 4H), 3.40 (s, 1H), 3.30 (s, 1H), 1.26 (t, J=7.2 Hz, 6H).

N,N-Dibutyl-4-[(1E,3E)-4-(thien-2-yl)-1,3-butadienyl] aniline (8). A solution of diethyl (thien-1-yl)methylphosphonate 7 (2.47 g, 10.5 mmol) and 3-(N,N-dibutylaminophenyl)-acrolein 3 (2.59 g, 10 mmol) in 20 mL of THF was cooled to 0° C. Potassium t-butoxide (1.35 g, 12 mmol) was added into the solution in three portions. The reaction mixture was stirred at 0° C. for 2 hours, warmed up to room temperature, stayed for 2 hours and quenched with 2 mL of water. THF was removed by rotary evaporation and the residue was purified via a flash chromatography on silica gel with a gradient eluent of hexanes to 5% ethyl acetate in hexanes to afford 2.87 g of product as viscous oil (84%).

N,N-Dibutyl-4-[(1E,3E)-4-(5-formylthien-2-yl)-1,3-butadienyl]aniline (9). A solution of N,N-Dibutyl-4-[(1E, 3E)-4-(thien-2-yl)-1,3-butadienyl]aniline 8 (2.87 g, 8.4 mmol) in 100 mL of THF was cooled to 0° C. 3.7 mL of n-butyl lithium (2.5 M, 9.3 mmol) was added dropwise. After this addition the solution was stirred for 1.5 hour at 0° C. The solution was treated with DMF (0.92 g, 12.6 mmol) in 2 mL of THF and stirred for 2 hours and warmed up to room temperature. After stirring for additional 1 hour, 1 mL of water was added to quench the reaction. The resulting mixture was stirred overnight to allow the completion of reaction. THF was removed via rotary evaporation, the residue was taken by 100 mL of water and extracted with 3×100 mL of dichloromethane. The combined organic layers were dried over Na$_2$SO$_4$ and concentrated. The crude product was purified via a flash chromatography on silica gel with a gradient eluent of hexanes to 15% ethyl acetate in hexanes to give 1.53 g of product (50%) as red oil.

Example 8

Preparation of a Representative Nonlinear Optically Active Compound: Amino Benzene Donor; Substituted Thiophene Bridge; Tricyanodihydrofuran Acceptor In this example, the preparation of a representative nonlinear optically active compound is described. The compound includes an amino benzene donor, substituted thiophene bridge, and tricyanodihydrofuran acceptor having a trifluoromethyl substituent. The preparation is illustrated schematically in FIG. 13.

A mixture of N,N-dibutyl-4-[(1E, 3E)-4-(3-tert-butyldimethylsiloxy-5-formylthien-2-yl)-1,3-butadienyl]aniline (102 mg, 0.2 mmol), prepared as described below, and 2-dicyanomethylene-3-cyano-4,5-dimethyl-5-trifluoromethyl-2,5-dihydrofuran (51 mg, 0.2 mmol) in 1 mL of ethanol was irradiated under focused microwave 20 W for 8 minutes. The resulting mixture was concentrated and purified through a flash chromatography on silica gel with a gradient eluent of hexanes/ethyl acetate (20/1–9/1) to give 85 mg of product as dark solid (57%). $^1$H NMR (CDCl$_3$) δ 8.07 (d, 15 Hz, 1H), 7.42 (s, 1H), 7.32 (d, 9.2 Hz, 2H), 6.95–7.09 (m, 1H), 6.65–6.76 (m, 3H), 6.59 (d, 9.0 Hz, 2H), 6.45 (d, 15.2 Hz, 1H), 4.69 (s, 2H), 3.30 (t, 7.4 Hz, 4H), 1.89 (s, 3H), 1.46–1.62 (m, 4H), 1.35 (sexi, 6.8 Hz, 4H), 0.95 (t, 7.4 Hz, 6H)0.92 (s, 6H), 0.11 (s, 9H).

Figure 14:
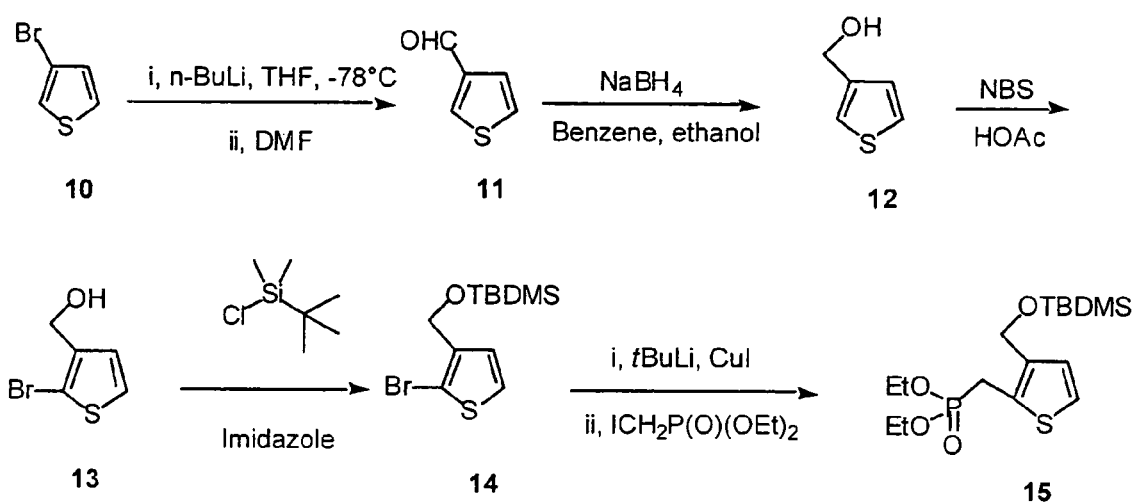
FIG. 14 is a schematic illustration of the preparation of a substituted thiophene useful in preparing a representative nonlinear optically active compound of the invention.
Figure 15:
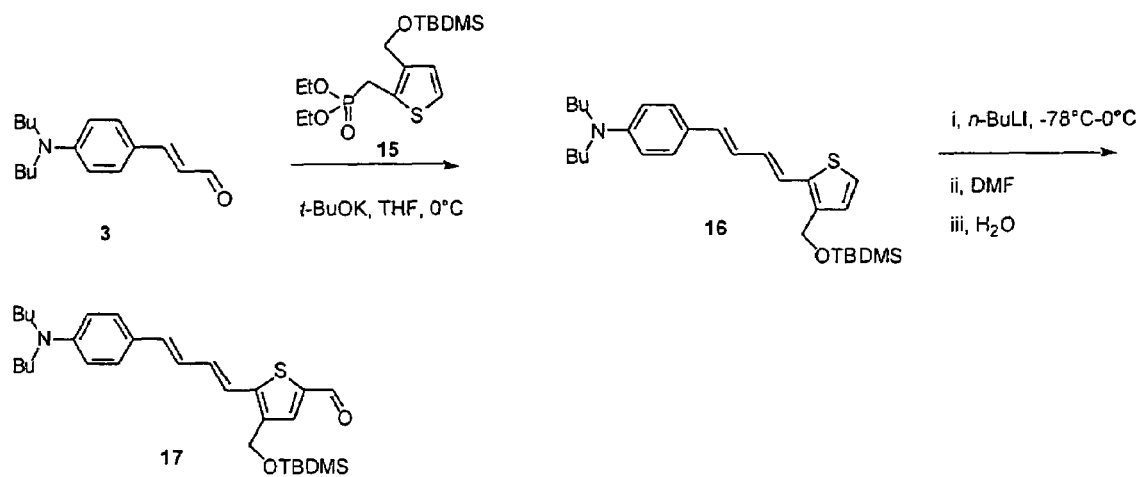
FIG. 15 is a schematic illustration of the preparation of a donor-bridge compound useful in preparing a representative nonlinear optically active compound of the invention.

N,N-Dibutyl-4-[(1E,3E)-4-(3-tert-butyldimethylsiloxy-5-formylthien-2-yl)-1,3-butadienyl]aniline. The synthetic scheme of conjugation building block, diethyl [2-(tert-butyldimethylsiloxymethyl)thien-1-yl]-methylphosphate 15, was shown in FIG. 14. 3-Bromothiophene 10 was formylated with n-BuLi/DMF to afford 3-thiophenecarboxaldehyde 11. Aldehyde 11 was reduced by sodium borohydride to afford 3-(hydroxymethyl)-thiophene 12 that was then brominated regioselectively by NBS in acetic acid to afford 2-bromo-3-hydroxymethylthiophene 13. The hydroxyl group on thiophene ring in 13 was protected with tert-butyldimethylsilyl chloride. Instead of using multi-step Arbuzov reaction to generate methylene phosphate on electro-rich thiophene ring, thienylmethylene phosphates 15 was obtained by one step nucleophilic substitution of diethyl iodomethylene phosphate with thienyl copper generated in-situ by the treatment of 2-bromo-3-(tert-butyldimethylsiloxymethyl) thiophene 14 with t-BuLi followed by copper (I) iodide. As shown in FIG. 15, Wittig-Homer-Emmons reaction of 3 and 15 afforded exclusively trans-configuration alkene 16, which was then formylated with n-BuLi/DMF to produce the desired aldehyde 17.

3-Thiophenecarboxaldehyde (11). A solution of 3-bromothiophene 10 (5.0 g, 30.7 mmol) in 30 mL of diethyl ether was cooled to −78° C., and then 13.5 mL of n-butyl lithium (2.5 M in hexane, 33.8 mmol) was added dropwise until a white turbid solution was formed persistently. The reaction mixture was stirred for 1 hour. A solution of DMF (3.36 g, 46 mmol) in 10 mL of diethyl ether was added dropwise over 15 minutes. After this addition the resulting mixture was kept at −78° C. for additional 30 minutes and then brought to room temperature. The reaction was allowed to complete during the next 45 minutes and then quenched by 1 mL of water. The resulting mixture was diluted by 100 ml of water and extracted with 3 ×100 mL of diethyl ether. The combined diethyl ether extracts were dried over Na$_2$SO$_4$ and concentrated via rotary evaporation. The residue was purified through a flash chromatography on silica gel with an eluent of dichloromethane/hexanes (½) to give 3.02 g of product (87.8%). 11 was used in the subsequent reaction without further characterization.

3-(Hydroxymethyl)thiophene (12). A solution of 3-thiophenecarboxaldehyde 11 (10 g, 89.3 mmol) in 20 mL of benzene and 20 mL of absolute ethyl alcohol was cooled to 0° C. and then sodium borohydride (4.39 g, 116 mmol) was added in three portions to the solution over an hour. After the addition, the reaction mixture was warmed up to room temperature and stirred for anther 3 hours and quenched with 3 mL of water. The solvent was evaporated and the residue was taken by 300 mL of dichloromethane and washed with 2×100 mL of water. The organic layer was dried over Na$_2$SO$_4$ and concentrated via rotary evaporation. The crude product was purified via a flash chromatography on silica gel with an eluent of dichloromethane/hexanes (1/1) to give 7.1 of pure product (70%). $^1$H NMR (CDCl$_3$) δ 7.28–7.32 (m, 1H), 7.20–7.22 (brm, 1H), 7.08 (dd, 4.4 Hz, 1.2 Hz, 1H), 4.68 (s, 2H), 1.74 (brm, 1H). Anal. C$_5$H$_6$OS require 52.60; H, 5.30. Found C, 53.89; H, 5.61.

2-Bromo-3-hydroxymethylthiophene (13). To a solution of 3-hydroxymethylthiophene 12 (4.06 g, 35.6 mmol) in 18 mL of acetic acid was added N-bromosuccinimide (6.34 g, 35.6 mol) at room temperature and stirred for 45 minutes. The resulting mixture was quenched with 1 mL of water, poured into 250 mL ether and washed with 100 mL of water, 100 mL of 10% NaHCO$_3$ aq. respectively. The organic layer was dried over Na$_2$SO$_4$ and concentrated. 6.25 g of crude product 13 (91%) was obtained and used for the subsequent reaction without further purification.

2-Bromo-3-(tert-butyldimethylsiloxymethyl)thiophene (14). tert-Butyldimethylsilyl chloride 13 (3.3 g, 22.1 mmol) in 2 mL of DMF was added into a solution of imidazole (3.13 g, 46 mmol) and 2-bromo-3-hydroxymethylthiophene 13 (3.55 g, 18.4 mmol) in 10 mL of DMF at 0° C. The reaction mixture was stirred at room temperature to subside heat by this exothermic reaction. After stirring for 22 hours, the resulting mixture was poured into 100 mL of cold water with crushed ice and extracted with 2×150 mL of dichloromethane. The organic layers were combined, dried over Na$_2$SO$_4$ and concentrated via rotary evaporation. Residual amount of DMF was removed in vacuo. The crude product was purified through a flash chromatography on silica gel with an eluent of hexane to give 3.96 g pure product as liquid (70%).

Diethyl [2-(tert-butyldimethylsiloxymethyl)thien-1-yl] methylphosphate (15). 74.3 mL of tert-butyl lithium (1.7 M in Pentane, 126.3 mmol) was added dropwise to a solution of 2-bromo-3-(tert-butyldimethylsiloxymethyl)thiophene 14 (17.64 g, 57.4 mmol) in 250 mL of THF at –78° C. After stirring at -78° C. for 2 hour, the resulting solution was transferred, via cannula, into a suspension containing copper (I) iodide (10.93 g, 57.4 mmol) in 20 mL of THF at ca. –40° C. The yellow mixture was stirred at 0° C. for 2 hours, treated with diethyl iodomethylphosphate (15.96 g, 57.4 mmol) in 40 mL of DMSO, and then warmed up to room temperature. The mixture with yellow precipitate was stirred for 24 hours at room temperature. After the completion of reaction, THF was removed via rotary evaporation and the residue was taken by 300 mL of water and 300 mL of diethyl ether. The organic layer was washed successively with 2×100 mL of water, 1×100 mL of 5% aqueous NaHCO$_3$, 2×100 mL of saturated brine solution. The organic layer was dried over Na$_2$SO$_4$ and concentrated. The black residue was purified through a flash chromatography on silica gel with a gradient eluent of hexanes/ethyl acetate (2/1–1/1) to afford diethyl [2-(tert-butyldimethylsiloxymethyl)thien-1-yl]methylphosphate 15 as clear yellow oil at the yield of and 8.96 g (47%). $^1$H NMR (CDCl$_3$) δ 7.09 (dd, 5.4 Hz, 2.8 Hz, 1H), 6.96 (d, 5.2 Hz, 1H), 4.65 (d, 2.8 Hz, 2H), 4.02 (q, 7 Hz, 4H), 3.39 (s, 1H), 3.28 (s, 1H), 1.24 (t, 7Hz, 6H), 0.88 (s, 9H), 0.05 (s, 6H).

N,N-Dibutyl-4-[(1 E,3E)-4-(3-tert-butyldimethylsiloxythien-2-yl)-1,3-butadienyl]aniline (16). A solution of diethyl [2-(tert-butyldimethylsiloxymethyl)thien-1-yl]methylphosphonate 15 (2.65 g, 7 mmol) and 3-(N,N-dibutylaminophenyl)acrolein 3 (1.89 g, 7.7 mmol) in 20 mL of THF was cooled to 0° C. Potassium tert-butoxide (0.808 g, 8.4 mmol) was added into the solution in three portions. The reaction mixture was stirred at 0° C. for 2 hours, warmed up to room temperature, stayed for 2 hours and quenched with 2 mL of water. THF was removed by rotary evaporation and the residue was purified via a flash chromatography on silica gel with a gradient eluent of hexanes to 5% ethyl acetate in hexanes to afford 2.97 g of product as a viscous oil (88%). $^1$H NMR (CDCl$_3$) δ 7.26 (d, 8.8 Hz, 2H), 7.02 (d, 5.2 Hz, 1H), 6.95 (d, 5 Hz, 1H), 6.62–6.71 (m, 4H), 6.57 (d, 9 Hz, 2H), 4.71 (s, 2H), 3.36 (t, 7.8 Hz, 4H), 1.45–1.51(m, 4H), 1.33 (sexi, 7.8 Hz, 4H), 0.93 (t, 7.2 Hz, 6H), 0.90 (s, 9H), 0.06(s, 6H).

N,N-Dibutyl-4-[(1E,3E)-4-(3-tert-butyldimethylsiloxy-5-formyl-thien-2-yl)-1,3-butadienyl]aniline (17). A solution of N,N-dibutyl-4-[(1E,3E)-4-(3-tert-butyldimethylsiloxythien-2-yl)-1,3-butadienyl]aniline 16 (2.42 g, 5 mmol) in 120 mL of THF was cooled to –78° C. 2.2 mL of n-butyl lithium (2.5 M, 5.5 mmol) was added dropwise. After this addition the solution was stirred for 1 hour each at –78° C. and at 0° C., respectively. The solution was re-cooled to –78 ° C. and treated with DMF (0.55 g, 6.8 mmol) in 2 mL of THF. The reaction mixture was stirred for 2 hours at –78° C. and warmed up to room temperature. After stirring for additional 2 hours, 0.5 mL of water was added to quench the reaction. The resulting mixture was stirred overnight to allow the completion of reaction. THF was removed via rotary evaporation, the residue was taken by 100 mL of water and extracted with 3×100 mL of dichloromethane. The combined organic layers were dried over Na$_2$SO$_4$ and concentrated. The crude product was purified via a flash chromatography on silica gel with a gradient eluent of hexanes to 5% ethyl acetate in hexanes to give 2.23 g of product (87%) as red oil. $^1$H NMR (CDCl$_3$) δ 9.76 (s, 1H), 7.29 (d, 9.2 Hz, 2H), 6.58–6.85 (m, 5H), 6.57 (d, 8.4 Hz, 2H), 4.71 (s, 2H), 3.27 (t, 7.8 Hz, 4H), 1.55 (br, 4H), 1.33 (sexi, 8.0 Hz, 4H), 0.94 (t, 7.0 Hz), 6H), 0.92 (s, 9H), 0.09 (s, 6H).

Example 9

Preparation of a Representative Nonlinear Optically Active Compound: Amino Benzene Donor; Substituted Thiophene Bridge; 2-(1'-Cyano-1'-nitro)methylene-2,5-dihydrofuran Acceptor In this example, the preparation of a representative nonlinear optically active compound is described. The compound includes an amino benzene donor, substituted thiophene bridge, and 2-(1'-cyano-1'-nitro)methylene-2,5-dihydrofuran acceptor. The preparation is illustrated schematically in FIG. 16.

A mixture of N,N-dibutyl-4-[(1E,3E)-4-(5-formylthien-2-yl)-1,3-butadienyl]aniline (250 mg, 0.68 mmol), prepared as described above in Example 7, and 2-(1'-cyano-1'-nitro) methylene-3-cyano-4,5,5-trimethyl-2,5-dihydrofuran 4 (200 mg, 0.91 mmol) in 0.3 mL of acetic anhydride was heated under microwave radiation at 20 W for 12 minutes. The resulting mixture was purified through a flash chromatography on silica gel with a gradient eluent of hexanes/ethyl acetate (20/1–3/1) to give 130 mg of product as dark solid (33%). $^1$H NMR (CDCl$_3$) δ 7.79 (d, 15.2 Hz, 1H), 7.41 (d, 4.0 Hz, 1H), 7.37–7.39 (m, 1H), 7.32 (d, 8.2 Hz, 2H), 7.01 (d, 4 Hz, 1H), 6.90–7.00 (m, 1H), 6.70–6.80 (m, 2H), 6.64 (d, 15.0 Hz, 1H), 6.59 (d, 8.4 Hz, 2H), 3.29 (t, 7.0 Hz, 4H), 1.79 (s, 3H), 1.57 (m, 4H), 1.34 (sexi, 7.6 Hz, 4H), 0.94 (t, 7.0 Hz, 6H).

Example 10

Electro-Optic Properties of Representative Nonlinear Optically Active Compounds

In this example, the electro-optic (E-O) properties of representative nonlinear optically active compounds is described.

To determine the macroscopic nonlinear optical property of representative compounds including a 2,5-dihydrofuran acceptor moiety, an E-O study was performed on a guest/host polymer system in which the compound described in Example 7 (23 wt %) was formulated in polymethylmethacrylate (PMMA) having a molecular weight of 15,000. The cyclopentanone solution of this guest/host polymer (14% solid content, filtered through 0.2 mm PTFE syringe filter) was spin coated onto half-etched ITO glass substrates at a spread of 500 rpm and spin rate of 1000 rpm. See, Mortazavi, M. A., et al., *Appl. Phys. B.* 53:287. 1991. The resulting film showed good optical quality with a thickness of 1.2 μm. The film sample was hard-baked under vacuum at 65° C. for more than 12 hours to ensure the removal of the residual solvent. Then a thin layer of gold was sputtered onto the film as the top electrode to perform the high electric field poling. Freshly prepared film sample was contact poled at 90° C. for 5 minutes with a DC electric field of 1.0 MV/cm under nitrogen atmosphere. See, Ma, H., et al., *Chem. Mater.* 11:2218, 1999. The E-O coefficient ($r_{33}$) value was measured using the simple reflection technique at 1.3 μm communication wavelength (see, Teng, C. C., et al., *Appl. Phys. Lett.* 56(18):30, 1990, and the poled film of the compound in PMMA showed a optimal $r_{33}$ value of 128 pm/V. To our knowledge, this value is among the highest reported for guest/host NLO polymers at 1.3 μm, which is more than four times that of $LiNbO_3$ (30 pm./V at 1.3 μm).

This poled PMMA film containing the compound retained up to 80% of its original $r_{33}$ value after 300 hours at room temperature and had a glass transition temperature of about 85° C. To improve the long term temporal stability of the poling-induced alignment of the compound, a polymer matrix with significant high glass transition temperature was used. Because the compound must be sufficiently stable to survive the higher poling temperature and have compatible miscibility in the polymer matrix to ensure the appropriate doped chromophore concentration without introducing phase separation, a polyquinoline based PQ-100 polymer was chosen due to its excellent electrical, mechanical, and thermal properties. Generally, highly polarizable compounds with large dipole moment (μ~13.5 Debye calculated by MOPAC for the compound) would incur severe inter-compound electrostatic interactions when compound was doped in matrix at higher concentration. See, (a) Shi, Y., et al., *Science* 288:119, 2000; (b) Chromophore dipole moment (,) was calculated by MOPAC package in a ChemDraw 3D ULTRA program from CambridgeSoft, Cambridge, Mass.

Figure 17:
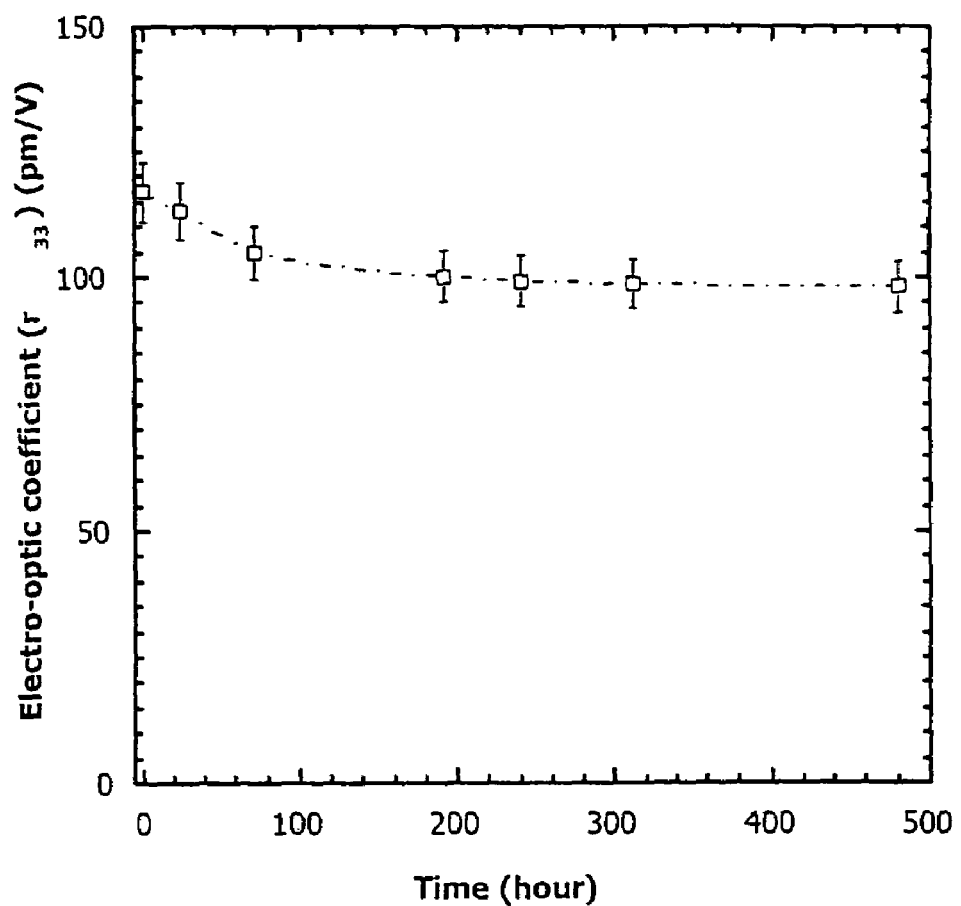
FIG. 17 is a graph illustrating the electro-optic coefficient as a function of time for a representative nonlinear optically active compound of the invention in a polymer host.

Compound shape modification by incorporating bulky side-chain group allows for the enhanced poling efficiency by isolating compounds from interacting with each other. Correspondingly, the compound described in Example 8 was synthesized by incorporating tert-butyldimethylsilyl (TB-DMS) onto the bridge moiety through a inert methylene linkage. Without interfering the electron distribution from donor to acceptor, this chemical modification leaves enough room for further optimization of the highest achievable E-O coefficients if higher compound concentration was supposed to be applied. To test the selected E-O guest/host polymer system for long-term temporal stability of poling-induced chromophore alignment, similar E-O polymer film was prepared from PQ-100 containing 26 wt % of the compound prepared in Example 8 in cyclopentanone solution. The glass transition temperature dropped from the original 265° C. (pristine PQ-100) to 140° C. due to the plasticization by the compound. After poling at 140° C. with 1 MV/cm for 5 minutes, an E-O coefficient of 116 pm/V was obtained at 1.3 μm. The temporal stability of the E-O signal was monitored at 85° C. under vacuum. After an initial quick relaxation, the E-O coefficient retained over 85% of its original value up to 480 hours. The electro-optic coefficient for the compound substituted with the TBDMS group in PQ-100 as a function of time is illustrated in FIG. 17.

Example 11

General Procedures

All chemical reagents were purchased from Aldrich and were used as received unless otherwise specified. Methylene chloride ($CH_2Cl_2$) was distilled over calcium hydride. Tetrahydronfuran (THF) and diethyl ether were distilled over sodium benzophenone ketyl under nitrogen. Dimethyl sulfoxide (DMSO) was distilled over calcium hydride. N,N-Dimethylformamide (DMF) and chloroform were dried over 5 Å molecule sieves. All reactions were carried out under inert nitrogen atmosphere unless otherwise specified. $^1$H NMR spectra (200 MHz) were taken on a Bruker-200 FT NMR spectrometer, all spectra were obtained in $CDCl_3$ (unless otherwise noted) at 18° C.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A dihydrofuran-containing compound having the structure:

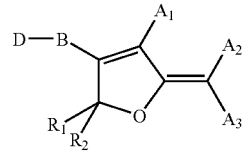

wherein D is a π-electron donor group;
wherein B is a π-electron conjugated bridge group that provides electronic conjugation from the donor group to the dihydrofuran group;
wherein $R_1$ is at least one of an aryl group or heteroalkyl group;
wherein $R_2$ is at least one of an aryl group or heteroalkyl group; or
wherein $R_1$ and $R_2$ taken together form a cycloalkyl group;
wherein $A_1$ is at least one of an alkyl group, an aryl group, or an electron withdrawing group;
wherein $A_2$ is an electron withdrawing group;
wherein $A_3$ is an electron withdrawing group;
wherein $A_1$, $A_2$ and $A_3$ are not all CN.

2. The compound of claim 1, wherein $R_1$ is at least one of phenyl, halogen-substituted phenyl, or alkyl-substituted phenyl.

3. The compound of claim 1, wherein $R_2$ is at least one of phenyl, halogen-substituted phenyl or alkyl-substituted phenyl.

4. The compound of claim 1, wherein $A_1$ is at least one of CN, $NO_2$, $SO_2CF_3$, 2-pyridinyl, 4-pyridinyl, trifluoromethylphenyl, perfluorophenyl, $SO_2Ph$ wherein Ph is an aryl group, or $CO_2R$ wherein R is an alkyl group.

5. The compound of claim 1, wherein $A_2$ is at least one of CN, $NO_2$, $SO_2CF_3$, or $CO_2R$ wherein R is an alkyl group.

6. The compound of claim 1, wherein $A_3$ is at least one of CN, $NO_2$, $SO_2CF_3$, or $CO_2R$ wherein R is an alkyl group.

7. A compound having the structure:

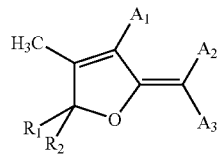

wherein $R_1$ is at least one of an aryl group or heteroalkyl group;
wherein $R_2$ is at least one of an aryl group or heteroalkyl group; or
wherein $R_1$ and $R_2$ taken together form a cycloalkyl group;
wherein $A_1$ is at least one of an alkyl group, an aryl group, or an electron withdrawing group;
wherein $A_2$ is an electron withdrawing group;
wherein $A_3$ is an electron withdrawing group;
wherein $A_1$, $A_2$ and $A_3$ are not all CN.

8. The compound of claim 7, wherein $R_1$ is at least one of phenyl, halogen-substituted phenyl, or alkyl-substituted phenyl.

9. The compound of claim 7, wherein $R_2$ is at least one of phenyl, halogen-substituted phenyl or alkyl-substituted phenyl.

10. The compound of claim 7, wherein $A_1$ is at least one of CN, $NO_2$, $SO_2CF_3$, 2-pyridinyl, 4-pyridinyl, trifluoromethylphenyl, perfluorophenyl, $SO_2Ph$ wherein Ph is an aryl group, or $CO_2R$ wherein R is an alkyl group.

11. The compound of claim 7, wherein $A_2$ is at least one of CN, $NO_2$, $SO_2CF_3$, or $CO_2R$ wherein R is an alkyl group.

12. The compound of claim 7, wherein $A_3$ is at least one of CN, $NO_2$, $SO_2CF_3$, or $CO_2R$ wherein R is an alkyl group.

* * * * *

UNITED STATES PATENT AND TRADEMARK OFFICE
CERTIFICATE OF CORRECTION

PATENT NO. : 7,078,542 B2  Page 1 of 1
APPLICATION NO. : 10/934964
DATED : July 18, 2006
INVENTOR(S) : K.-Y. Jen et al.

It is certified that error appears in the above-identified patent and that said Letters Patent is hereby corrected as shown below:

| COLUMN | LINE | ERROR |
| --- | --- | --- |
| 32 (Claim 7, | 2 line 12) | after "group;" insert --and-- |
| 32 (Claim 10, | 11-12 lines 2-3) | "trifluorom-ethylphenyl," should break --trifluoro-methylphenyl,-- |

Signed and Sealed this

Twenty-fourth Day of October, 2006

JON W. DUDAS
*Director of the United States Patent and Trademark Office*

UNITED STATES PATENT AND TRADEMARK OFFICE
CERTIFICATE OF CORRECTION

PATENT NO. : 7,078,542 B2
APPLICATION NO. : 10/934964
DATED : July 18, 2006
INVENTOR(S) : K.-Y. Jen et al.

It is certified that error appears in the above-identified patent and that said Letters Patent is hereby corrected as shown below:

| COLUMN | LINE | ERROR |
|---|---|---|
| 32 (Claim 7, | 2 line 12) | after "group;" insert --and-- |
| 32 (Claim 10, | 11-12 lines 2-3) | "trifluorom-ethylphenyl," should break --trifluoro-methylphenyl,-- |

Signed and Sealed this

Fourteenth Day of November, 2006

JON W. DUDAS
*Director of the United States Patent and Trademark Office*